(12) United States Patent
Hoffman et al.

(10) Patent No.: US 12,161,763 B2
(45) Date of Patent: Dec. 10, 2024

(54) FORMULATION AND METHOD FOR INCREASING ORAL BIOAVAILABILITY OF DRUGS

(71) Applicant: Yissum Research Development Company of the Hebrew University of Jerusalem Ltd., Jerusalem (IL)

(72) Inventors: Amnon Hoffman, Jerusalem (IL); Abraham J. Domb, Efrat (IL); Anna Elgart, Mevaseret Zion (IL); Irina Cherniakov, Gan Yavne (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 124 days.

(21) Appl. No.: 16/577,609

(22) Filed: Sep. 20, 2019

(65) Prior Publication Data
US 2020/0009067 A1    Jan. 9, 2020

Related U.S. Application Data

(62) Division of application No. 14/371,819, filed as application No. PCT/IL2013/050047 on Jan. 17, 2013, now abandoned.

(60) Provisional application No. 61/704,893, filed on Sep. 24, 2012, provisional application No. 61/696,540, filed on Sep. 4, 2012, provisional application No. 61/615,457, filed on Mar. 26, 2012, provisional application No. 61/588,341, filed on Jan. 19, 2012.

(51) Int. Cl.
| | |
|---|---|
| *A61K 9/51* | (2006.01) |
| *A61K 9/00* | (2006.01) |
| *A61K 9/10* | (2006.01) |
| *A61K 9/127* | (2006.01) |
| *A61K 31/05* | (2006.01) |
| *A61K 31/17* | (2006.01) |
| *A61K 31/343* | (2006.01) |
| *A61K 31/352* | (2006.01) |
| *A61K 31/366* | (2006.01) |
| *A61K 31/436* | (2006.01) |
| *A61K 31/7048* | (2006.01) |
| *A61K 36/67* | (2006.01) |
| *A61K 38/00* | (2006.01) |
| *A61K 45/06* | (2006.01) |
| *A61K 47/14* | (2017.01) |
| *A61K 47/22* | (2006.01) |
| *A61K 47/24* | (2006.01) |

(52) U.S. Cl.
CPC .......... *A61K 9/5123* (2013.01); *A61K 9/0019* (2013.01); *A61K 9/10* (2013.01); *A61K 9/127* (2013.01); *A61K 31/05* (2013.01); *A61K 31/17* (2013.01); *A61K 31/343* (2013.01); *A61K 31/352* (2013.01); *A61K 31/366* (2013.01); *A61K 31/436* (2013.01); *A61K 31/7048* (2013.01); *A61K 36/67* (2013.01); *A61K 45/06* (2013.01); *A61K 47/14* (2013.01); *A61K 47/22* (2013.01); *A61K 47/24* (2013.01); *A61K 38/00* (2013.01)

(58) Field of Classification Search
None
See application file for complete search history.

(56) References Cited

U.S. PATENT DOCUMENTS

| | | |
|---|---|---|
| 5,439,891 A | 8/1995 | Kapil et al. |
| 5,536,506 A | 7/1996 | Majeed et al. |
| 5,616,593 A | 4/1997 | Patel et al. |
| 5,744,161 A | 4/1998 | Majeed et al. |
| 5,972,382 A | 10/1999 | Majeed et al. |
| 7,732,404 B2 | 6/2010 | Domb et al. |
| 7,919,113 B2 | 4/2011 | Domb |
| 8,101,274 B2 | 1/2012 | Spedden |
| 2006/0148727 A1 | 7/2006 | Hendrix |
| 2007/0104741 A1* | 5/2007 | Murty ............ A61K 47/22 424/400 |
| 2007/0160675 A1* | 7/2007 | Devane et al. |
| 2009/0232887 A1 | 9/2009 | Odidi et al. |
| 2009/0324703 A1 | 12/2009 | Frautschy et al. |
| 2009/0324727 A1 | 12/2009 | Foguet Roca |
| 2010/0041622 A1 | 2/2010 | Bromley et al. |
| 2012/0027693 A1 | 2/2012 | Bean et al. |
| 2016/0206585 A1* | 7/2016 | Hustvedt ............ A61K 47/10 |

FOREIGN PATENT DOCUMENTS

| | | |
|---|---|---|
| EP | 0 810 868 B1 | 8/2001 |
| EP | 1 938 801 A1 | 7/2008 |
| EP | 2 228 062 A1 | 9/2010 |
| WO | 03/049753 A1 | 6/2003 |

(Continued)

OTHER PUBLICATIONS

Amidon et al. "A theoretical basis for a biopharmaceutic drug classification: the correlation of in vitro drug product dissolution and in vivo bioavailability." Pharm Res., Mar. 1995., vol. 12, No. 3, pp. 413-420.

(Continued)

*Primary Examiner* — David J Blanchard
*Assistant Examiner* — Sarah J Chickos
(74) *Attorney, Agent, or Firm* — Vorys, Sater, Seymour and Pease LLP; Anthony P. Venturino; Maryellen Feehery Hank

(57) ABSTRACT

Provided is a formulation and method for increasing bioavailability of an orally administered drug.

17 Claims, 16 Drawing Sheets

(56) References Cited

FOREIGN PATENT DOCUMENTS

| WO | 2007/103435 | A2 | 9/2007 |
|---|---|---|---|
| WO | 2008/065451 | A2 | 6/2008 |
| WO | 2008/077641 | A1 | 7/2008 |
| WO | 2008/095122 | A2 | 8/2008 |
| WO | 2009/052491 | A2 | 4/2009 |
| WO | 2010/010431 | A1 | 1/2010 |
| WO | 2012/063182 | A1 | 5/2012 |

OTHER PUBLICATIONS

Atal et al. "Scientific evidence on the role of Ayurvedic herbals on bioavailability of drugs." J Ethnopharmacol., Sep. 1981, vol. 4, No. 2, pp. 229-232.

Bano et al. "Effect of piperine on bioavailability and pharmacokinetics of propranolol and theophylline in healthy volunteers." Eur J Clin Pharmacol., 1991., vol. 41, No. 6, pp. 615-617.

Bekerman et al. "Cyclosporin nanoparticulate liposphere for oral administration." J Pharm Sci., May 6, 2004, vol. 93, No. 5, pp. 1264-1270.

Da Silva et al. "Opposite effects of iv amiodarone on cardiovascular vagal and sympathetic efferent activities in rats." Am J Physiol Regulatory Integrative Comp Physiol., May 6, 2002, pp. R543-R548.

Elgart et al. "Liposphere and pro-nano liposphere for delivery of poorly water soluble compounds." Chemistry and Physics of Lipids., 2012, pp. 438-453.

Hoffman et al. "Kinetics of drug action in disease states. XXIX. Effect of experimental nephrotic syndrome on the pharmacodynamics of heptabarbital: implications of severe hypoalbuminemia." J Pharmacol Exp Ther., Apr. 1989, vol. 249, No. 1, pp. 117-122.

Janakiraman et al. "Studies of Effect of Piperine on Oral Bioavailability of Ampicillin and Norfloxacin." Afr. J. Trad. CAM, 2008, pp. 257-262, vol. 5, No. 3.

Johnson et al. "Enhancing the bioavailability of resveratrol by combining it with piperine." Mol Nutr Food Res., Jun. 2011, vol. 55, No. 8, pp. 1169-1176.

Koul et al. "Structure-activity relationship of piperine and its synthetic analogues for their inhibitory potentials of rat hepatic microsomal constitutive and inducible cytochrome P450 activities." Bioorg Med Chem., Jan. 2000, vol. 8, No. 1, pp. 251-268.

Kulkarni et al. "Antidepressant activity of curcumin: involvement of serotonin and dopamine system." Psychopharmacology (Berl)., Sep. 3, 2008, vol. 201, No. 3, pp. 435-442.

Lipinski et al. "Experimental and computational approaches to estimate solubility and permeability in drug discovery and development settings." Adv Drug Deliv Rev., Mar. 1, 2001, vol. 46, Nos. 1-3, pp. 3-26.

Minton, Barbara. "Substance in Black Pepper Increases Nutrient Absorption up to Two Thousand Percent." naturalnews.com, Nov. 17, 2008, 3 pages.

Mujumdar et al. "Effect of piperine on pentobarbitone induced hypnosis in rats." Indian J Exp Biol., May 1990, vol. 28, No. 5, pp. 486-487.

Mujumdar et al. "Anti-inflammatory activity of piperine." Japan J Med Sci Biol., Jun. 1990, vol. 43, No. 3, pp. 95-100.

Mujumdar et al. "Effect of Piperine on Bioavailabilty of Oxyphenylbutazone in Rats." Indian Drugs., Feb. 1999, pp. 123-126, vol. 36, No. 2.

Patil et al. "Role of Piperine as a Bioavailability Enhancer." International Journal of Recent Advances in Pharmaceutical Research., Oct. 2011, vol. 4, pp. 16-23.

Pattanaik et al. "Effect of piperine on the steady-state pharmacokinetics of phenytoin in patients with epilepsy." Phytother Res., Aug. 2006, vol. 20, No. 8.

Pattanaik et al. "Pharmacokinetic interaction of single dose of piperine with steady-state carbamazepine in epilepsy patients." Phytother Res., Sep. 2009, vol. 23, No. 9, pp. 1281-1286.

Shoba et al. "Influence of piperine on the pharmacokinetics of curcumin in animals and human volunteers." Planta Med., May 1998, vol. 64, No. 4, pp. 353-356.

Veerareddy et al. "Pharmacokineties and tissue distribution of piperine lipid nanospheres." Pharmazie, 2008, vol. 63, pp. 352-355.

Zhang et al. "Nano-based Drug Delivery System Enhances the Oral Absorption of Lipophilic Drugs with Extensive Presystemic Metabolism" Current Drug Metabolism., 2012, vol. 13, No. 8, pp. 1110-1118.

Jun. 6, 2013 International Search Report issued in International Application No. PCT/IL2013/050047.

* cited by examiner

FORMULATION AND METHOD FOR INCREASING ORAL BIOAVAILABILITY OF DRUGS

FIELD OF THE INVENTION

The present invention pertains to a formulation and method for increasing the oral bioavailability of drugs by utilizing advanced pro-nano liposphere (PNL) and PNL incorporating piperine.

BACKGROUND OF THE INVENTION

Many dispersion systems are currently in use as, or being explored for use as carriers of substances, particularly biologically active compounds. These systems are designed to protect the substance from the environment during delivery and to provide a controlled release of the substance to a targeted area. In some cases, the goal is to target specific sites in the body using the dispersion. In other cases, the goal is to prepare a drug carrier system that acts as a reservoir at the site of injection. Dispersion systems used for pharmaceutical and cosmetic formulations can be categorized as either suspensions or particles ranging in size from a few nanometers up to hundreds of microns, dispersed in an aqueous or non-aqueous medium using suspending agents. Solid particles include microspheres, microcapsules, nanoparticles and nanospheres.

One of the in situ methods of preparation of liposheres with a particle size below 100 nanometers was developed by using a dispersible pre-concentrate system [1]. This delivery system, termed pro-nanoliposphere (LIPOSPHERES), is based on a solution containing a drug, a triglyceride, a phospholipid and other additives, in a mixture of common surfactants, and an organic solvent that is miscible with all components. This solution spontaneously forms nanoparticles when in an aqueous media, and even in vivo, e.g., the upper GI lumen content.

U.S. Pat. No. 7,919,113 [2] discloses dispersible concentrate preparations (nano-liposheres) for the solubilization of lipophilic drugs to enhance the bioavailability of water insoluble drugs.

When given orally, a drug is absorbed into the enterocyte monolayer in the basolateral side of the intestine, where it can undergo metabolism and/or efflux back into the lumen by trans-membranal transporters. From the apical side of the entrocytes the drug is delivered via the portal vein to the liver and thereafter into the systemic blood circulation. Bioavailability is defined as the fraction of an administered dose of unchanged drug that reaches the systemic circulation. By definition, when a medication is administered intravenously, its bioavailability is 100%.

Research in the field of drug absorption has focused on ways to increase drug efficacy by increasing drug absorption. To this end, methods have been used to increase drug absorption using liposomes as carriers and by designing more lipophilic drugs. However, these methods have not been successful in circumventing liver biotransformation and biliary secretion of drugs.

Thus, when a medication is orally administered, its bioavailability generally decreases due to incomplete absorption and first-pass metabolism and also may vary from patient to patient. Bioavailability is one of the essential tools in pharmacokinetics, as it must be considered when calculating dosages for none intravenous routes of administration.

Despite the great advancements in the area of various drug delivery systems such as nano-liposheres, many drugs are prone to poor oral bioavailability due to biological barriers at the enterocyte level, termed "intestinal first pass metabolism". These biological processes include Phase I metabolism, namely oxidative enzymes, and Phase II metabolism including conjugation, sulphation and glucuronidation by intestinal enzymes. In addition, the poor oral bioavailability is attributed to efflux transporters e.g. permeability-glycoprotein (P-gp) at the enterocyte luminal membrane [3].

P-gp can efflux out a variety of drugs from cells which ultimately lead to unsuccessful drug therapy. It also affects various pharmacokinetic parameters of drugs, such as P-gp substrates like absorption, distribution, metabolism and excretion from the body which leads to modified bioavailability and possible adverse drug reactions. Thus, it is believed that the P-glycoprotein efflux pump prevents certain pharmaceutical compounds from transversing the mucosal cells of the small intestine and, therefore, from being absorbed into the systemic circulation.

Knowledge of the approaches to circumvent P-gp efflux pump is critical for targeted drug therapy and formulation design and development of dosage forms. It is established that drugs and excipients interact with P-gp in a complicated procedure and information of its mechanism of interaction are still unclear.

While there are several methods to inhibit metabolic and efflux processes by pharmacological agents, there are limited pharmaceutical solutions to overcome this problem. Much more difficult is the case of Phase II metabolism, where there are currently no effective technologies that control this biological process in the clinical setting.

Piperine is an alkaloid responsible for the pungency of black pepper (*Piper nigrum*), and long pepper (*Piper longum*), along with chavicine (an isomer of piperine). The active compound in both *Piper longum* and *Piper nigrum* is piperine (1-piperoyl piperidine), which has been shown to possess bioavailability enhancing activity with various structurally and therapeutically diverse drugs. It has been found that piperine bioavailability-enhancing property may be attributed to increased absorption, which may be due to alteration in membrane lipid dynamics and change in the conformation of enzymes in the intestine [4].

Kulkarni S K, et al., [5] examined the antidepressant effect of curcumin with piperine and concluded that the combination of piperine (2.5 mg/kg, i.p., 21 days), with curcumin (20 and 40 mg/kg, i.p.) showed significant potentiation of its anti-immobility, neurotransmitter enhancing and monoamine oxidase inhibitory (MAO-A) effects as compared to the effect curcumin alone.

Pattanaik S, et al., [6] examined the effect of simultaneous administration of piperine (20 mg, p.o.) on plasma concentration of carbamazepine (300 mg or 500 mg), twice daily, in epileptic patients and found that piperine significantly increased the mean plasma concentrations of carbamazepine in both dose groups.

U.S. Pat. No. 5,439,891 [7] discloses that the active constituent of *Piper longum* and *Piper nigrum*, piperine, was shown to increase bio-availability of certain anti-tubercular and anti-leprosy drugs like rifampicin, isoniazid, pyrazinamide, ethambutol and dapsone.

U.S. Pat. No. 5,616,593 [8] discloses use of piperine to improve bioavailability of substances used to treat disease of cardiovascular system, central nervous system, gastrointestinal treatment or hemopoetic system.

U.S. Pat. No. 5,536,506 [9] and U.S. Pat. No. 5,972,382 [10] disclose compositions and methods for the improvement of gastrointestinal absorption and systemic utilization of nutrients and nutritional supplements, wherein the compositions comprise a minimum of 98 percent of pure alkaloid piperine.

REFERENCES

[1] Bekerman, T., J. Golenser, and A. Domb. *J Pharm Sci.*, 93(5): 1264-70, 2004.
[2] U.S. Pat. No. 7,919,113.
[3] Lipinski, C. A., et al., *Adv Drug Deliv Rev.*, 46(1-3): p. 3-26, 2001.
[4] PATIL UK, *International Journal of Recent Advances in Pharmaceutical Research*, 4:16-23, October 2011.
[5] Kulkarni S. K., Bhutani M. K., Bishnoi M *Psychopharmacology* (*Berl*), 201:435-442, 2008.
[6] Pattanaik S, et al., *Phytother Res.* 23(9):1281-6, 2009. doi: 10.1002/ptr.2676.
[7] U.S. Pat. No. 5,439,891.
[8] U.S. Pat. No. 5,616,593.
[9] U.S. Pat. No. 5,536,506.
[10] U.S. Pat. No. 5,972,382.
[11] Koul S, et al. *Bioorg Med Chem.*, 8(1):251-68, 2000.

SUMMARY OF THE INVENTION

The present invention is concerned with optimization of drug bioavailability. It is the purpose of the present application to provide a superior nano-particulate formulation, e.g., delivery system, for enhancing the oral bioavailability of a broad range of drugs, having a low oral bioavailability, by combining its administration with pro-nano lipospheres (PNLs) or with PNL loaded piperine (herein referred to in short as piperine-PNL). The PNL or piperine-PNL technology enhances the oral bioavailability of drugs, in particular lipophilic drugs, which bioavailability is limited not only due to Phase I metabolism and/or P-gp efflux but also due to direct Phase II metabolism in the intestine.

The inventors of the present invention have developed a PNL and piperine-PNL systems that has multiple concerted productive activities that altogether synergistically enhances bioavailability of poor bioavailable drugs and results in more stable, and less variable, absorption of the drugs from the gastrointestinal tract and thereby also to a reduction of the required dose of the drug.

The development of piperine-PNL is based on a PNL pro-nano-dispersion system which employs an orally administered mixture of lipids, surfactants and co-solvent, herein referred to as a "dispersible concentrate". This concentrate may be administered orally in combination with an active agent which is administered either within the pro-nanodispersion formulation or provided shortly before or after the administration of the PNL dosage unit (e.g. soft gelatin capsule). Thus, when reaching the aqueous phase of the gastro intestinal (GI) tract, the PNL is released and spontaneously forms drug encapsulated nano-particles with a particle diameter of 500 nm or less.

The piperine-PNL utilizes this concept and in a synergistic manner with piperine, a natural food derived component and adds to the absorption enhancement properties of the PNL disclosed in U.S. Pat. No. 7,919,113 [2], herein incorporated by reference.

Furthermore, due to piperine's poor aqueous solubility and fairly good lipid solubility, it can be readily incorporated into the lipid PNL core. Incorporating piperine into PNL presents an opportunity to manipulate the critical systems accounted for the marked first pass effect of various drugs (e.g. cannabidiol and tetrahydrocannabinol). The incorporation of piperine increases the piperine's concentration that reaches the intestine and the liver, and potentially competitively inhibits the drugs' metabolism in those metabolic sites. As a result the oral bioavailability of the various drugs could be further enhanced as compared to the administration of the drugs in PNL not containing piperine.

As known to a person of skill in the art, the increase in drug bioavailability is defined as an increase in the Area Under the Curve (AUC); being the integrated measure of systemic drug concentrations over time, in units of mass-time/volume. The AUC from time zero (the time of dosing) to time infinity (when no drug remains in the body) following the administration of a drug dose is a measure of the exposure of the patient to the drug.

The inventors of the present invention have surprisingly found that administration of cannabidiol (CBD) in piperine-PNLs resulted in significantly higher oral relative bioavailability in comparison to administration of cannabidiol in PNLs without piperine. Oral administration of CBD-piperine-PNL resulted in significantly higher AUC and $C_{max}$ values by 5 fold and 15 fold, respectively, as compared to control, (as further described hereinbelow) attesting to the increase in the oral bioavailability of drugs that is attributed to the piperine-PNLs system of the present invention.

Thus, in one aspect of the present invention, there is provided a composition (formulation or a drug delivery system) for oral administration of at least one drug, said composition comprising:

a) a dispersible concentrate, characterized by being capable of forming, upon contact with an aqueous solution, particles of a size of less than about 500 nm, said dispersible concentrate comprising:
  (i) at least one surfactant;
  (ii) at least one solid component at room temperature; and
  (iii) an amphiphilic solvent;
b) an amount of at least one piperine, piperine analog or isomer thereof, e.g., in an amount sufficient to increase the bioavailability of said composition.

The "dispersible concentrate" is a composition which spontaneously forms a nano-particulate dispersion in an aqueous medium, for example in water upon dilution, or in the gastric juices after oral administration. The "dispersible concentrate" includes those compositions that form solid particles having a mean diameter of less than about 500 nm upon contact with an aqueous medium.

The "aqueous medium," refers to a water based medium, i.e., a liquid medium in which water is the major component. In accordance with the present invention, the aqueous medium may be the digestive fluid formed in the stomach (e.g., gastric fluid formed by cells lining the stomach), GI tract fluids or any liquid medium, in vivo or ex vivo in which the herein defined dispersible concentrate is dissolved.

The "surfactant" is any amphiphilic compound generally recognized in the art as having surface active qualities. Surfactants generally include anionic, cationic, nonionic, and zwitterionic compounds, as further described herein. In some embodiments, the surfactant is a combination of at least one high HLB (hydrophilic/lipophilic balance) surfactant having an HLB of at least about 8, with at least one surfactant being a low HLB surfactant having an HLB of less than about 5.

In some embodiments, the surfactant is selected from polyoxyethylene, sorbitanmonolaurate, sorbitanmonooleate and mixtures thereof.

In other embodiments, the composition further comprises an ethoxylated fat and fatty compounds. Some non-limiting examples being selected from polyethyleneglycol-hydrogenated castor oil (e.g. cremophor and cremophor RH).

In still other embodiments, the composition further comprises a phospholipid selected from an egg phospholipid, a soy phospholipid and lecithin of various grades and purities.

In still yet other embodiments, the composition further comprises a fatty acid ester, e.g., a fatty acid ester that is a solid fat at room temperature such as tricaprin.

In some embodiments, the composition of the present invention is of a particle size that is less than about 200 nm.

In other embodiments, the composition is of a particle size that is less than about 100 nm.

In still other embodiments, the composition is of a particle size that is less than about 50 nm.

As used herein, the term "solid component" refers to solid materials that are solid at room temperature (defined herein as 25° Celcius) and that dissolve in the dispersible concentrate and which upon dispersion in aqueous medium becomes part of the formed solid nanoparticles.

Some non-limiting examples of solid components, in accordance with the present invention include fatty acids, fatty amines and fatty alcohols or their respective esters or amides that melt at a temperature above 25° C.; polymers that are solids at 25° C., and paraffins and waxes that are solid at 25° C.

In some embodiments, the fatty acid esters are selected from mono-, di-, and triglycerides and fatty acid esters with long and short chain alcohols that are solids at 25° C. In other embodiments, the solid components are selected from tricaprin, trilaurin, trimyristine, tripalmitin, tristearin and mixtures thereof that are solids at 25° C.

In still other embodiments, the solid components are compounds that solidify in situ upon dispersion in aqueous medium, e.g., partially or fully hydrogenated vegetable oil that are solid at 25° C.

The "amphiphilic solvent" utilized in a composition of the invention is selected from lower alkyl (having between 1 and 8 carbon atoms) esters of lactic acid, lower alkyl (having between 1 and 8 carbon atoms) lactone esters and N-methylpyrrolidone. Some non-limiting examples of lower alkyl esters include methyl, ethyl, propyl, isopropyl, butyl, hexyl, pentyl and octyl esters.

In some embodiments, the amphiphilic solvent is selected from methyl lactate, ethyl lactate, propyl lactate, spironolactone and N-methylpyrrolidone.

In some embodiments, the amphiphilic solvent is a combination of a lower alkyl ester of lactic acid with N-methylpyrrolidone.

In some embodiments, the amphiphilic solvent comprises a combination of a solvents selected from the family of lower alkyl esters of lactic acid together with a solvent selected from the family of alkyl lactone esters or N-methylpyrrolidone.

In other embodiments, the amphiphilic solvent is combined with a hydrophilic organic solvent such as ethylene glycol, glycofurol or PEG 400.

As known, "Piperine" is (E,E)1-[5-(1,3-benzodioxyl-5-yl)-1-oxo-2,4-pentadenyl] piperidine being the main constituent of many *Piper* species. In accordance with the present invention, piperine may be obtained commercially or from a number of species of peppers from the Piperaceae family (e.g., *Piper nigrum, P. longum, P. tuberculatum, P. hancei, P. hispidum, P. retrofactum, P. attenuatum, P. genueense, P. chaba, P. aurantiacum, P. auritum, P. cubeba, P. peltatum, P. umbellatum* and *P. mystheticum, P. nigrum*).

In some embodiments, piperine utilized in accordance with the invention is obtained from *Piper longum* or *Piper nigrum*.

In other embodiments, piperine utilized in accordance with the invention is in pure form (e.g. piperine at a purity of >95%).

In other embodiments, piperine is a piperine analog (e.g., derivatives in which the piperidine ring is substituted, e.g., by an amino group, or an ester group (e.g., $C_{1-6}$ alkyl esters) of metabolites containing an OH group as described, for example in Koul S, et al. [11]. The piperine analogues may be synthetically obtained or produced from a natural source.

In other embodiments, piperine is a piperine isomer (e.g. chavicine)

In some embodiments, the amount of piperine in the composition of the invention is in the range of about 0.1 to about 10 mg/kg body weight.

In accordance with the present invention, the piperine, piperine analog or isomer thereof may or may not be incorporated into the pro-nano lipospheres formed upon contact of the dispersible concentrate with an aqueous solution and may also be partially incorporated into said lipospheres.

The composition comprising piperine (and/or a piperine analog or isomer thereof) and referred to in short as piperine-PNL is also related to hereinafter as an empty composition, as compared to a composition comprising a drug (described hereinbelow).

The increase in drug bioavailability attributable to administration of the piperine, as described herein, can be determined by measuring total systemic drug concentrations over time after administration of a composition comprising piperine and the drug as compared to after administration of the drug alone, defined as an increase in the Area Under the Curve (AUC) as described hereinabove.

Thus, when the piperine, piperine analog or isomer thereof are used in sufficient amounts in the composition of the present invention, the activity of P-gp and Cytochrome $P_{450}$ 3 A4 (abbreviated CYP3A4) is reduced.

The sufficient amounts of piperine, piperine analog or isomer thereof are the amounts necessary to elevate the systemic concentrations of the drug over time and can be determined by measuring total systemic drug concentrations as readily recognized by the skilled artesian.

The increase in drug bioavailability achieved by the use of the composition of the invention and by practicing the methods described herein also results in reduction in inter-individual and intra-individual variation in oral bioavailability of the drug, enabling the practitioner to better standardize drug administration regimens using the piperine-PNL system of the present invention.

In some embodiments, the empty composition as defined herein comprises at least one drug.

The "drug" is generally any chemical capable of administration to a mammal, which modifies or alters the mammal's physiology. Thus, in accordance with the present invention the "drug" is any substance intended for use in the treatment or prevention of disease or a disorder. Drugs include synthetic and naturally occurring substances as well as recognized pharmaceuticals, such as those listed in the United States Pharmacopeia, (USP36 NF31, 2013: U.S. Pharmacopoeia National Formulary United States Pharmacopeial Convention 36th Edition 2012; ISBN 978-3769258844).

In some embodiments, the drug is a lipophilic compound or a mixture of two or more different lipophilic compounds.

As used herein, the "lipophilic compound" is a compound that in its non-ionized form is more soluble in lipid or fat than in water.

In some embodiments, the lipophilic compound is a compound having a LOG P≥2 (Log P being an estimate of a compound's overall lipophilicity as recognized by the skilled artesian).

The lipophilic compounds, as described herein, are generally compounds which have limited oral bioavailability due to first pass metabolism, by (1) Phase I metabolic enzymes e.g. CYP3A4 (2) intra-enterocytes phase II metabolic enzymes (e.g. UDP-glucuronosyltransferases, sulfotransferases, N-acetyltransferases, glutathione S-transferases and methyltransferases; (3) efflux from the enterocytes back to the gastrointestinal lumen by efflux pumps (responsible for the export of many lipophilic and ampiphilic drugs that impedes their intracellular absorption) such as P-gp (that is extensively distributed and expressed in the intestinal epithelium), and thus are associated with poor and variable oral bioavailability In some embodiments, the lipophilic compounds are compounds categorized as Class II of the Biopharmaceutical Classification System (BCS) proposed by Amidon, G. L., et al. *Pharm Res.*, 12(3):413-20, 1995. BCS is an experimental model that measures permeability and solubility under prescribed conditions. BCS Class II compounds are considered to have low solubility and high permeability and Class IV compounds characterized as having low solubility and low permeability.

Some non-limiting examples of lipophilic compounds that are subjected to both CYP3A4 and P-gp efflux include amiodarone, tacrolimus, cannabidiol, cyclosporine, indinavir, nicardipine, quinidine and verapamil.

Some non-limiting examples of compounds that are subjected to intestinal CYP3A4 metabolism and which are not subjected P-gp efflux substrates include felodipine, midazolam, nifedipine and propafenone.

Some non-limiting examples for compounds subjected to P-gp efflux and which are not subjected to CYP3A4 metabolism substrates are talinolol and fexofenadine.

In some embodiments, the lipophilic compound is a BCS Class IV compound (e.g. hydrochlorothiazide, amphothericin B).

Examples for additional poorly water soluble compounds with oral bioavailability affected by intestinal and hepatic first pass metabolism and subjected to P-gp efflux are amlodipine, diltiazem, felodipine, nicardipine, nifedipine, nimodipine, nisoldipine, verapamil, sirolimus, tacrolimus, atorvastatin, lovastatin, simvastatin, fexofenadine, buspirone, carbamazepine, pimozide, midazolam, triazolam, albendazole, itraconazole, cisapride, colchicine, sildenafil, amphotericine B, steroids, polyphenols and canbinoids.

In some embodiments, the lipophilic compound is a nutraceutical, a food product or a homeopathic agent (e.g., polyphenols, carotenoids, cyclopsporine).

In other embodiments, the drug is a lipophilic compound or a mixture of at least two lipophilic compounds.

In some embodiments, the lipophilic compound is Amiodarone.

In other embodiments, the lipophilic compound is Tacrolimus.

In still other embodiments, the lipophilic compound is Talinolol.

In still yet other embodiments, the lipophilic compound is cyclosporine A.

In additional embodiments, the lipophilic compound is a cannabinoid, a derivative or a synthetic analog thereof, or a mixture of cannabinoids. Some non-limiting examples of cannabinoids are tetrahydrocannabinol, cannabidiol (CBD), cannabinol, cannabigerol, tetrahydrocannabivarin, cannabidivarin and cannabichromene.

In accordance with the present invention, when the composition comprises a drug, as defined herein, the drug may or may not be incorporated into the pro-nano liposheres formed upon contact of the dispersible concentrate with an aqueous solution and may also be partially incorporated into said liposheres.

In some embodiments, the composition of the invention further comprises a pharmaceutically acceptable carrier and/or excipient, which physiologically tolerable and do not typically produce an allergic or similar untoward reaction, such as gastric upset, dizziness and the like, when administered to a mammal such as a human.

The composition of the present invention (either empty composition or composition comprising a drug) is a composition suitable for administration by the oral route (e.g. buccal, sublabial, sublingual) using a swallowable capsule or any other medicament formed in a relatively stable shell (e.g. soft gel capsule, pill, tablet, granule).

In some embodiments, the composition and drug are administered in the same pharmaceutical formulation, i.e., in a single unit dosage form.

In other embodiments, the composition and drug are administered in a different pharmaceutical formulation, i.e., in a separate unit dosage form.

In accordance with the present invention, the herein defined composition may also be diluted or combined in a food or beverage prior to feeding to a subject.

In another aspect of the present invention there is provided a method for increasing the bioavailability of a drug, the method comprising orally co-administering to a mammal (human or non-human) in need of treatment by said pharmaceutical drug:

(1) said drug, and (2) an empty composition, according to the present invention, wherein said at least one piperine, piperine analog or isomer thereof being present in said composition in a sufficient amount to provide bioavailability of said drug greater than bioavailability of said drug in the absence of said at least one piperine, piperine analog or isomer thereof.

The herein described method can be used to modify the pharmacokinetics of drugs by multiple mechanisms, including inhibition of phase I and phase II metabolism, in the intestine and in the liver and intestinal inhibition of P-gp efflux pumps.

In some embodiments, the empty composition is co-administered substantially simultaneously with the drug (either less than 20 min. before, less than 20 min after or together with the drug).

In other embodiments, the empty composition and drug are sequentially administered.

The term "sequentially" or "sequentially administered" as used herein is intended to mean that an empty composition is administered before one or more subsequently administered drugs or that the drug is administered before the empty composition.

In some embodiments, the empty composition is administered 0 minutes, 20 minutes, before the subsequently administered drug.

In other embodiments, the drug is administered 0 minutes, 20 minutes, before the subsequently administered empty composition.

In some embodiments, the drug is administered in at least one dose within 24 hrs after administration of the dose of the empty composition; i.e., the empty composition is not administered again before or with every administration of the drug, but may be administered intermittently during the course of treatment.

In some embodiments, when the drug is administered before the empty composition, clinical evaluation of the drug's effect (e.g. on a disease state) and of the drug's plasma concentration are measured (e.g. using methods well-established as common practice in the art) and based on said measured parameters, a decision of the amount of empty composition to be administered thereafter or before the administration of the drug, is made. According to such embodiments, depending on the type of disease to be treated, the condition of the patient or any other parameters that are readily apparent to the skilled artesian, the amount of empty composition to be administered and/or amount of piperine in said empty composition are determined.

Thus, in accordance with the present invention, the empty composition and drug may be administered together, alternately or intermittently in all of the various aspects of the invention, depending on the type of drug, the type of disease to be treated with the drug and/or any other considerations that are readily apparent to skilled artesian.

In still another aspect of the present invention, there is provided a process for preparing the composition of the invention, said process comprising:

(a) dissolving the amphiphilic solvent and optionally phospholipid (and optionally gently heating to achieve complete dissolution of the phospholipid), (b) adding at least one surfactant to the solution obtained in step (a) (and optionally gently heating and stirring to obtain a homogenous solution.

In some embodiments, said process further comprises a step (c) of adding the drug (e.g. as a powder) to the pre-concentrate formed in step (b) and optionally gently heating (e.g. at between about 30° C. and between about 50° C.) and stirring to obtain a homogenous solution which upon gentle agitation in aqueous phase, spontaneously forms drug encapsulated nano-dispersion.

When a piperine comprising composition is desired, piperine (e.g. as a powder) may be added with the drug.

In some embodiments, the ratio of amphiphilic solvent and phospholipid in step (a) of said process is between 8 and 1, respectively.

In some embodiments, the ratio of amphiphilic solvent and phospholipid I step (a) of said process is about 8:1, respectively.

The present invention also contemplates the use of the composition of the invention for the preparation of a medicament for increasing the bioavailability of a drug.

The medicament may include pharmaceutically acceptable carriers, for example, vehicles, adjuvants, excipients, or diluents, which are well-known to those who are skilled in the art and are readily available to the public. It is preferred that the pharmaceutically acceptable carrier be one which is chemically inert to the piperine-PNL and active drug and one which has no detrimental side effects or toxicity under the conditions of use.

Medicament formulations suitable for oral administration may comprise (a) liquid solutions, such as an effective amount of the composition dissolved in a non-aqueous diluent; (b) capsules, sachets, tablets, lozenges, and troches, each containing a predetermined amount of the composition, as solids or granules; (c) powders; (d) suspensions in an appropriate non-aqueous liquid; and (e) suitable non-aqueous emulsions. Liquid formulations may include diluents, such as alcohols, for example, ethanol, benzyl alcohol, and the polyethylene alcohols, either with or without the addition of a pharmaceutically acceptable surfactant, suspending agent, or emulsifying agent. Capsule forms may be of the ordinary hard- or soft-shelled gelatin type containing, for example, surfactants, lubricants, and inert fillers, such as lactose, sucrose, calcium phosphate, and corn starch. Tablet forms may include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms may comprise the composition in a flavor, usually sucrose and acacia or tragacanth, as well as pastilles comprising the composition in an inert base, such as gelatin and glycerin, or sucrose and acacia, emulsions, gels, and the like containing.

In another one of its aspects the present invention provides the use of the composition of the invention for increasing the bioavailability of a drug.

In still another one of its aspects the present invention provides the use of the composition of the invention for the preparation of a medicament for the treatment of at least one disease and/or disorder.

In an additional aspect, the present invention provides the composition of the invention for use in the treatment of at least one disease and/or disorder.

The present invention also contemplate the use of the composition of the invention for treating at least one disease and/or disorder In some embodiments, the disease is a disease treatable with at least one cannabinoid and/or a derivative thereof.

The "disease treatable with at least one cannabinoid or a derivative thereof" generally refers to a disease or disorder selected from intractable cancer pain, neuropathic and chronic pain, postoperative pain, rheumatoid arthritis, multiple sclerosis and spasticity, fibromialgia, inflammation, gastrointestinal disorders (e.g. nausea and vomiting, motility disorders), acute schizophrenia, cancer, tics and behavioral problems experienced by patients with tourette's syndrome, parkinson's disease, huntington's disease, diabetes and diabetic complications, cerebrovascular disorders and glaucoma.

The term "treatment" or any lingual variation thereof is used herein to denote treating the disease, disorder or condition, or ameliorating, alleviating, reducing, or suppressing symptoms of the disease, or slowing or stopping the progress of the disease.

In still another one of its aspects, the present invention provides the use of the composition of the invention in combination with other therapeutic modalities.

As used herein, the terms "therapeutic modalities", generally refers to any therapeutic agent, treatment or protocol/method that can be used in the treatment or alleviation of a disease or disorder or at least one symptom thereof.

In some embodiments, the therapeutic modality is selected from chemotherapy, hormonal therapy, radiation therapy, surgery, biological therapy and immunotherapy.

In some embodiments, the therapeutic modality is a non-drug therapy.

Thus, according to this aspect of the invention, a subject may be administered with a therapeutic agent (pertaining to the other therapeutic modality) in accordance with the therapeutic regimen that is dictated by said other therapeutic modality while the composition of the invention may be sequentially or substantially simultaneously administered in single or in multiple unit dosage forms.

In accordance with the present invention, the administration of the therapeutic agent pertaining to said other therapeutic modality can be carried out by any appropriate route including, but not limited to, oral routes, intravenous routes, intramuscular routes or any other administration route that is suitable to achieve the desirable effect of the other therapeutic modality.

In some embodiments, the composition of the invention is used to treat at least one symptom of a disease or disorder treated by said other therapeutic modality. For example, when the disease is cancer and the therapeutic modality is indicated to eradicate the cancer, the herein defined composition may be used to treat the pain symptoms associated with the cancer.

In other embodiments, the composition of the invention is used as an add-on (adjuvant) therapy to said other therapeutic modality to augment the treatment of the disease or disorder to be treated by said other therapeutic modality. In accordance with such embodiments the administration of the composition of the invention together with said other therapeutic modality results in more efficacious treatment (e.g. shortening of the time period to achieve remission, treatment and/or amelioration) of the disease or disorder treated with said other therapeutic modality than would have been obtained without the administration of the composition of the invention.

Generally, when used in an add-on therapy, the composition of the invention is administered less than 24 hours after the initiation of treatment with said other therapeutic modality.

By yet another aspect, the present invention provides a kit for oral administration of the composition of the invention, said kit comprising:
a) an empty composition as defined herein;
b) instructions of use.

In some embodiments, the herein defined kit further comprises at least one drug, as defined herein.

The components composed in any of the kits of the invention, may be contained in a single vessel or holding unit or in separate vessels and contain a label attached to or packaged with the container that describes the contents of the vessels and provides indications and/or instructions regarding administration of contents of the vessels to a mammalian subject in need of treatment with said kit(s). The kit form is particularly advantageous when the components are contained in different vessels for administration in different dosage amounts or when titration of the individual components of the kit (e.g., dispersible concentrate, piperine and drug) is desired by the prescribing physician.

The present invention also provides a composition for oral administration of at least one drug, said composition comprising a dispersible concentrate, characterized by being capable of forming, upon contact with an aqueous solution, particles of a size of less than about 500 nm, said dispersible concentrate comprising:
(i) at least one surfactant;
(ii) at least one solid component at room temperature; and
(iii) an amphiphilic solvent.

It should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
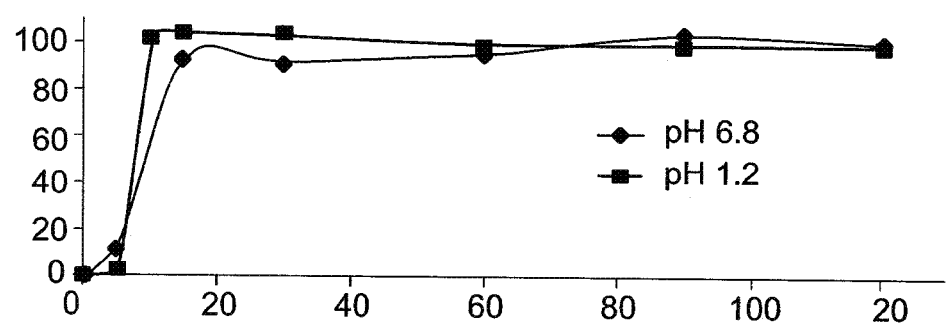
FIG. 1 presents comparative dissolution profile of AM (Amiodarone) nano liposheres containing soft gelatin capsules at pH 6.8 and 1.2 (n=3 for each pH).

The present invention is thus based on the realization that it is possible to increase the oral bioavailability of a drug, such as a drug containing a lipophilic compound, by administering the drug in a composition comprising pro-nano liospheres incorporating piperine.

The following specific examples illustrate various aspects of the present invention, and are not intended to be limiting in any way. For all examples, all the ingredients were dissolved in the solvent using magnetic stirrer, and heated gently (~40-45° C.) for 15-45 minutes until the ingredients were completely dissolved. To obtain particles, the concentrate formulation was diluted in at least 10 volumes of water in aqueous solution.

For all experiments described below, the particle size of the diluted formulation was measured with VLA particle size analyzer (Coulter N4 MD Submicron Particle Size Analyzer), suitable for submicron particle size determination. About 75 µl of the concentrate formulation were added to five milliliters of water. The particle size of the diluted formulation did not change when it dispersed in five milliliters of 0.1N HCl solution. For all experiments described below, unless otherwise stated, the active pharmaceutical ingredient (API) was in the base form (and not in the salt form).

Preparation of a Composition According to the Invention

The composition containing amiodarone HCl or tacrolimus, solvent, TRC (tricaprin) or alternatively TRL (trilaurin), egg phospholipid (Avanti, USA), Tween™ 20, SPAN™ 80 and Cremophor™ was prepared as given in Table 1 (all amounts of ingredients, in Table 1 as well as in the following tables, are given in milligrams). All compositions had a particle size of less than 100 nm. The particle size decreased as the amount of either ethyl lactate or Poly Ethylene Glycol (PEG) 400 was increased. Ethyl lactate was generally more effective than Poly Ethylene Glycol (PEG) 400 for providing smaller size particles.

TABLE 1

Amiodarone Pre-concentrate Basic Formulations

| Ingredient | 1 | 2 | 3 | 4 | 5 | 6 |
|---|---|---|---|---|---|---|
| Amiodarone HCL | 10 | 10 | 10 | 10 | 20 | 20 |
| Tricaprin | 40 | — | 40 | — | — | 52 |
| Trilaurin | — | 40 | — | 40 | 52 | — |
| Egg phospholipids | 40 | 40 | 40 | 40 | 20 | 20 |
| Tween™ 20 | 60 | 60 | 60 | 60 | 52 | 52 |
| SPAN™ 80 | 40 | 40 | 40 | 40 | 52 | 52 |
| Cremophor™ | 52 | 20 | 20 | 20 | 52 | 52 |
| Ethyl lactate | 160 | 160 | — | — | 190 | 180 |
| Poly Ethylene Glycol (PEG) 400 | — | — | 160 | 160 | — | — |

Effect of Various Hydrophobic Pharmaceutical Active Ingredients (API) and Vitamins on Particle Size Different compositions containing various hydrophobic Pharmaceutical Active Ingredients (API) and Vitamins were prepared as described in Tables 2A and 2B. The effect of the API's on the particle size when dispersed in water was examined Briefly, the droplet size of compositions which included hydrophobic API had small particle sizes (less than 100 nm) in cases of low API concentration but the particle size was increased in cases that the API concentration was higher (and was above 100 nm in some cases). Similar phenomenon was received with the vitamins.

Other hydrophobic API's and Vitamins were also tested and similar results were obtained (not shown in the next table). In all cases, the pharmaceutical active ingredient (API) was in the base form (and not in the salt form).

TABLE 2A

Formulations of various hydrophobic API in different amounts

| Ingredient | 1 | 2 | 3 | 4 | 5 | 6 | 7 | 8 | 9 | 10 |
|---|---|---|---|---|---|---|---|---|---|---|
| Trilaurin | 40 | 40 | 40 | 40 | 40 | 40 | 40 | 40 | 40 | 40 |
| Egg phospholipids | 20 | 20 | 20 | 20 | 20 | 20 | 20 | 20 | 20 | 20 |
| SPAN™ 80 | 40 | 40 | 40 | 40 | 40 | 40 | 40 | 40 | 40 | 40 |
| Tween™ 20 | 40 | 40 | 40 | 40 | 40 | 40 | 40 | 40 | 40 | 40 |
| Cremophor™ | 40 | 40 | 40 | 40 | 40 | 40 | 40 | 40 | 40 | 40 |
| Ethyl lactate | 140 | 140 | 140 | 140 | 140 | 140 | 140 | 140 | 140 | 140 |
| Soltanol | 20 | 40 | — | — | — | — | — | — | — | — |
| Flecaininde | — | — | 20 | 40 | — | — | — | — | — | — |
| Propafenone | — | — | — | — | 20 | 40 | — | — | — | — |

TABLE 2A-continued

Formulations of various hydrophobic API in different amounts

| Ingredient | 1 | 2 | 3 | 4 | 5 | 6 | 7 | 8 | 9 | 10 |
|---|---|---|---|---|---|---|---|---|---|---|
| Ezetimibe | — | — | — | — | — | — | 20 | 40 | — | — |
| Doxorudicin | — | — | — | — | — | — | — | — | 20 | 40 |

TABLE 2B

Formulations of various hydrophobic API and Vitamins in different amounts

| Ingredient | 1 | 2 | 3 | 4 | 5 | 6 | 7 | 8 | 9 | 10 |
|---|---|---|---|---|---|---|---|---|---|---|
| Trilaurin | 40 | 40 | 40 | 40 | 40 | 40 | 40 | 40 | 40 | 40 |
| Egg phospholipids | 20 | 20 | 20 | 20 | 20 | 20 | 20 | 20 | 20 | 20 |
| SPAN™ 80 | 40 | 40 | 40 | 40 | 40 | 40 | 40 | 40 | 40 | 40 |
| Tween™ 20 | 40 | 40 | 40 | 40 | 40 | 40 | 40 | 40 | 40 | 40 |
| Cremophor™ | 40 | 40 | 40 | 40 | 40 | 40 | 40 | 40 | 40 | 40 |
| Ethyl lactate | 140 | 140 | 140 | 140 | 140 | 140 | 140 | 140 | 140 | 140 |
| Sildenafil | 20 | 40 | — | — | — | — | — | — | — | — |
| Tadalafil | — | — | 30 | 60 | — | — | — | — | — | — |
| Vardenafil | — | — | — | — | 20 | 40 | — | — | — | — |
| Maxiletine | — | — | — | — | — | — | 20 | 40 | — | — |
| Vitamin D2 | — | — | — | — | — | — | — | — | 40 | — |
| Vitamin D3 | — | — | — | — | — | — | — | — | — | 40 |

Amiodarone HCL Pre-Concentrate Formation

The final Amiodarone HCL composition was based on preliminary formulation optimization studies and selected according to optimal solubilization capacity of the active ingredient and smallest particle size obtained upon dilution in aqueous phase, as described above. Initially amphiphilic co-solvent (ethyl lactate) and phospholipid (lecithin) at the ratio of 8:1 respectively were placed in a clean scintillation tube and heated to 40° C. until the lecithin was completely dissolved. Then triglyceride (trilaurin), polyoxyl 40-hydroxy castor oil, Tween 20, and Span 80 at the ratio of 1:1:1:1 were added; the mixture was gently stirred and heated to 45° C. until a homogenous solution was formed. Further, Amiodarone HCL powder was added, forming the AM pre-concentrate containing 3% AM. This pre-concentrate was gently stirred and heated to 45° C. till homogenous solution was formed. Upon gentle agitation in aqueous phase, this pre-concentrate spontaneously forms drug encapsulated O/W nano-emulsion. Amiodacre® ampoules content (50 mg/ml Amiodarone HCl, 20.2 mg/mL benzyl alcohol and 100 mg/mL Tween 80 in water) was used as control AM throughout all in-vivo and in-vitro studies.

Talinolol pre-concentrate was prepared by the same method as amiodarone HCL pre-concentrate, except for the different triglyceride that was used. For the preparation of the pre-concentrate a triglyceride; lecithin was used. The concentration of the compound i.e. talinolol in the pre-concentrate was 1%.

Blank pre-concentrate was prepared by the same method as miodarone HCL preconcentrate, except no active ingredient was added.

Tacrolimus nano liposheres were prepared by the same method to produce preconcentrate containing 5% tacrolimus. Prograf® capsules were used as control tacrolimus throughout in-vivo studies.

Cannabidiol (CBD) Nano Liposheres

CBD nano liposheres formulation was prepared by preconcentrate preparation method. The final nano liposheres composition was based on preliminary formulation optimization studies and selected according to optimal solubilization capacity of the active ingredient and smallest particle size obtained upon dilution in aqueous phase. Prior to adding active ingredient, two kinds of mixtures were prepared. The first is a mixture of amphiphilic co-solvent (ethyl lactate) and phospholipid (lecithin) at the ratio of 8:1, respectively. The second is a mixture of a triglyceride (tricaprin), polyoxyl 40-hydroxy castor oil, Tween 20, and Span 80 at the ratio of 1:1:1:1. Both mixtures were gently stirred and heated to 40° C. till homogenous solutions were formed. Both mixtures were added at the ratio of 1:1 w/w to a clean scintillation tube containing CBD powder, forming the CBD nano liposheres preconcentrate containing 3% CBD. This pre-concentrate was gently stirred and heated to 40° C. till homogenous solution was formed. Upon gentle agitation in aqueous phase, this pre-concentrate spontaneously forms drug encapsulated O/W nanoemulsion. CBD solution in Propylen Glycol/EthOH/Water 30/30/40 respectively was used as control throughout all in-vivo studies.

Characterization of the Formulations

The mean particles diameter, zeta potential and polydispersity index of the formed formulations by 1:10 dilution of the pre-concentrate in water are listed in Table 3. Amiodarone HCL, talinolol, tacrolimus, CBD and blank formulations were administered to animals by 1:10 dilution of the pre-concentrate in water. Thus, the characterizations were AM assessed following this dilution.

TABLE 3

The mean particles diameter, zeta potential and polydispersity index of the formed formulations by 1:10 dilution of the pre-concentrate in water

| Formulation | Size (d · nm) | Zeta potential (mv) | Pdi |
|---|---|---|---|
| Amiodarone HCL | 10 | 35.2 | 0.48 |
| CBD | 26 |  | 0.07 |
| Talinolol | 45 | 5.9 | 0.45 |
| Blank | 52 | 13.2 | 0.38 |

Drug Release Studies

Soft gelatin capsules containing AM nano-liposheres (0.5 g) were assessed for in-vitro release using standard USP 24 method, apparatus II (paddles) equipment (Caleva ST7, G.B. Caleva Ltd., Dorset, UK). A stirring speed of 75 rpm was used at 370 C in 500 ml of release medium (either pH 6.8 or pH 1.2). At predetermined time points samples of the release medium (0.5 mL) were withdrawn and analyzed by HPLC (analytical methods section) for AM content. Gastric buffer pH 1.2 was prepared as following: 250 ml of NaCL 0.2M were mixed with 425 ml of HCL 0.2M then distilled water was added to make a total volume of 1 L. Duodenal buffer pH 6.8 was prepared as following: 112 ml of NaOH 0.1 M were mixed with 250 ml of potassium dehydrogenphosphate then distilled water was added to make a total volume of 1 L.

Emulsification Time Study

To assess the self-emulsification properties, the emulsification time of the pro nanoliposheres was evaluated according to United States Pharmacopeia (USP) XXIII, dissolution apparatus II (Caleva ST7, G.B. Caleva Ltd., Dorset, UK). Briefly, 0.5 mL of the pro nano-liposheres was added drop wise to 500 mL of distilled water at 37° C. Gentle agitation was provided by a standard stainless steel dissolution paddle rotating at 50 rpm. The emulsification time was visually assessed as previously reported.

Emulsification Time and Drug Release Results

In both tested pH environments, pro nano-lipospheres presented similar dissolution profile, where the drug was entirely released within about 10 minutes (FIG. 1). The emulsification time obtained for pro nano-lipospheres was ~10 sec.

In-Vivo PK Studies

Animals:

Male Wistar rats weighing 300-350 g were used for the in vivo PK and ex vivo permeability studies. The project adhered to the principles of Laboratory Animal Care. All animals were deprived of food but not water 12 h prior to the experiments. All surgical and experimental procedures were reviewed and approved by the Animal Experimentation Ethics Committee of the Hebrew University Hadassah Medical School Jerusalem. An indwelling cannula was placed in the right jugular vein of each animal for systemic blood sampling, by a method described by Hoffman, A. and G. Levy., *J. Pharmacol Exp Ther.*, 249(1):117-22, 1989.

Amiodarone (AM) Bioavailability Studies

AM nano-lipospheres were freshly prepared 30 min before each experiment, by vortex-mixing 1 mL of the pre-concentrate in 9 mL water pre-heated to 37 C0 for 30 sec. The obtained AM concentration was 3 mg/mL. AM nano-lipospheres (12.5 mg/kg) were administered to the animals by oral gavage (n=6). The control group received 12.5 mg/kg AM solution prepared from Amiodacore® ampoules content (AM 50 mg/mL) dissolved in water to obtain 5 mg/mL concentration (n=6). Systemic blood samples (0.35 mL) were taken at 5 min pre-dose, 0.5, 1 2, 4, 8, 12, 24, 36 and 48 h post-dose.

For tacrolimus bioavailability studies, tacrolimus nano-lipospheres were freshly prepared 30 min before each experiment, by vortex-mixing 1 ml of the pre-concentrate in 9 ml water pre-heated to 37 C0 for 30 sec. The obtained concentration was 0.5 mg/ml. tacrolimus nano-lipospheres (1 mg/kg) were administered to the animals by oral gavage (n=6). The control group received 1 mg/kg tacrolimus suspension prepared from Prograf® capsules content suspended in water to obtain 0.5 mg/ml concentration (n=6). Systemic blood samples (0.3 ml) were taken at 5 min predose, 0.25, 0.5, 0.75, 1, 1.5, 2, 4, 8, and 12 h post-dose.

For talinolol relative bioavailability studies: nano-lipospheres were freshly prepared 30 min before each experiment, by vortex-mixing of the pre-concentrate in water (1:9) pre-heated to 37 C0 for 30 sec. The obtained talinolol concentration was 1 mg/mL. Talinolol nano-lipospheres (4 mg/kg) were administered to the animals by oral gavage (n=6). The control group received 4 mg/kg talinolol dissolved in PEG400:water:ethanol 25:60:15 to obtain 1 mg/mL concentration (n=6).

For CBD relative oral bioavailability studies, nano lipospheres was freshly prepared 30 min before each experiment, by vortex-mixing of the pre-concentrate in water (1:9) pre-heated to 37 C0 for 30 sec. The obtained CBD concentration was 3 mg/mL. CBD nano lipospheres (15 mg/kg) was administered to the animals by oral gavage (n=6). The control group received (15 mg/kg) CBD solution in propylene glycol/EthOH/water 30/30/40 respectively (1 mg/mL) (n=6).

Systemic blood samples (0.35 mL) were taken at 5 min pre-dose, 20 min, 40 min, 1 h 1.3 h, 1.6 h, 2 h, 3 h and 4 h post-dose.

AM PK Results

Figure 2:
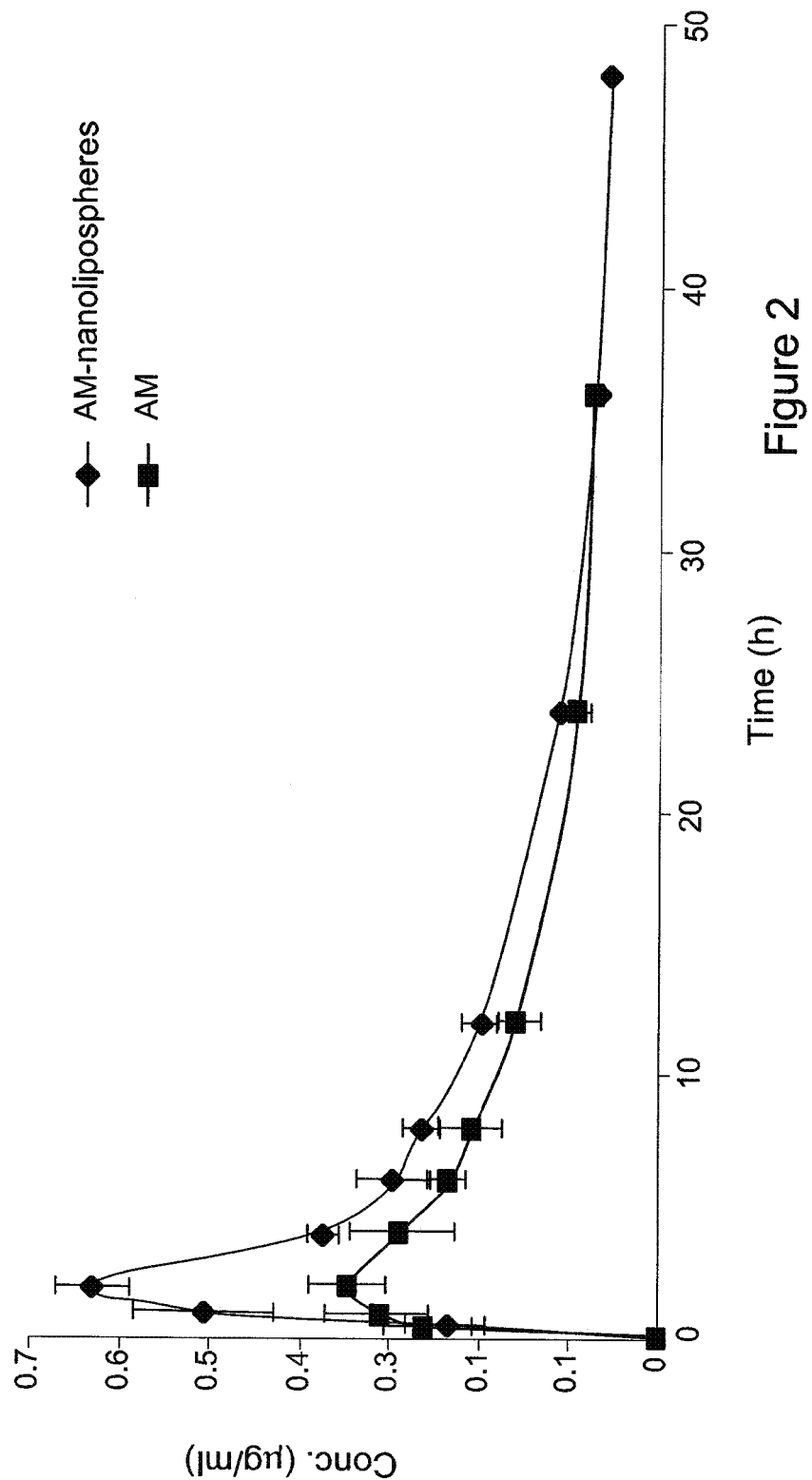
FIG. 2 presents plasma AM concentration-time plot (mean±S.E.M.) following PO administration of AM and AM-nano-liposheres, 12.5 mg/kg (n=6 for each group).

The plasma concentration time profiles for AM and AM-nano-lipospheres following oral administration of dose equivalent to 12.5 mg/kg AM are shown in FIG. 2. The corresponding AUC and $C_{max}$ parameters obtained in these in vivo experiments are listed in Table 4. The bioavailability of AM nano-lipospheres was significantly greater in comparison to AM alone. Similar results were obtained for the $C_{max}$ values.

Another finding is that the erratic absorption that characterizes Amiodarone becomes more regular when the drug is administered in the nano-formulation. The reduced fluctuations in $C_{max}$ are of high importance since Amiodarone is characterized by narrow therapeutic window and life-threatening side effects. Reduction of such fluctuations may improve the safety of Amiodarone therapy. In addition, the overall dose reduction which may be achieved by higher bioavailability might result in reduction of side effects of this drug.

Tacrolimus PK Results

Figure 3:
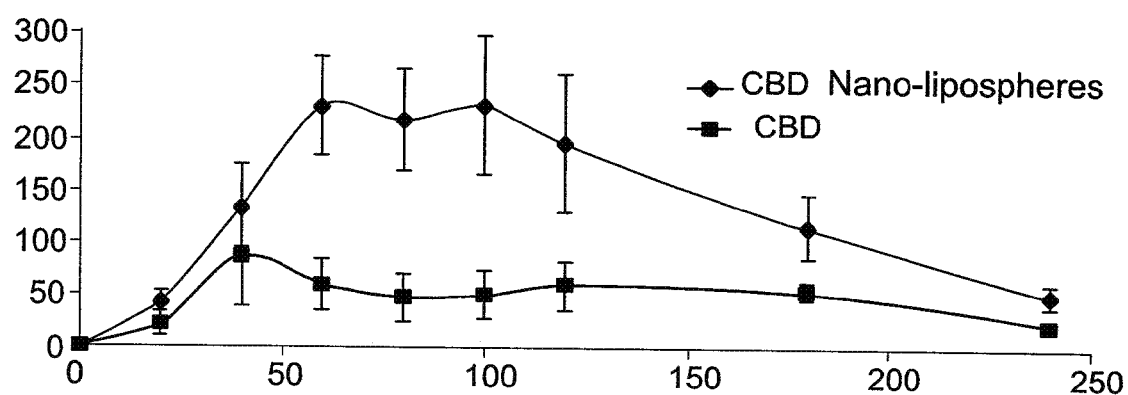
FIG. 3 present plasma CBD concentration-time plot (mean±S.E.M.) following PO administration of CBD and CBD nano liposheres, 12.5 mg/kg (n=6 for each group).

The tacrolimus concentration vs. time plot following oral administration of the drug alone or compounded in nano-lipospheres (1 mg/kg) is presented in FIG. 3, and the derived PK parameters are presented in Table 6.

The bioavailability of tacrolimus nano-lipospheres was significantly greater in comparison to tacrolimus alone. Similar results were obtained for the $C_{max}$ values.

Table 5 clearly demonstrates the reduced variability in plasmas tacrolimus concentrations obtained following tacrolimus-nano-lipospheres administration. Table 5 represents the coefficient of variation (% CV) in various time points during two hours following administration.

TABLE 4

PK parameters derived from PO administration of tacrolimus and tacrolimus - SNEDDS 1 mg/kg (n = 5 for each group).

| Cmax (ng/mL) | AUC (hr*/ng/mL) | |
|---|---|---|
| 14.7 ± 4/11 | 40.8 ± 10.6 | tacrolimus |
| 23.8 ± 2.66(*) | 69.4 ± 8.96(*) | Tacrolimus- nano lipospheres |

(*)Significant difference (p < 0.05) from tacrolimus corresponding value is found.

TABLE 5

Coefficient of variation (% CV) in various time points during two hours following oral administration of tacrolimus and tacrolimus - nano-lipospheres 1 mg/kg (n = 5 for each group).

| tacrolimus | tacrolimus-nano-lipospheres | time (h) |
|---|---|---|
| 95.1 | 31.5 (*) | 0.25 |
| 90.8 | 35.8 (*) | 0.5 |
| 73.2 | 9.1 (*) | 0.75 |
| 83.5 | 22.0 (*) | 1 |
| 70.5 | 30.7 (*) | 1.5 |
| 103.5 | 45.4 (*) | 2 |

(*) Significantly lower % CV than the corresponding values at the same time point in the group that received tacrolimus alone.

These findings demonstrate that Amiodarone and tacrolimus bioavailability increases not only when it is encapsulated in nano-lipospheres, but even the simultaneous presence of empty (i.e. drug-less) nano-lipospheres in the intestine. Moreover, encapsulation into nano-lipospheres reduces the high variability in plasma concentrations, typical for Amiodarone, tacrolimus and other BCS class II compounds.

CBD PK Results

The plasma concentration time profiles for CBD and CBD nano lipospheres following oral administration of 15 mg/kg CBD to rats are shown in FIG. 3. The corresponding AUC and $C_{max}$ parameters obtained in these in vivo experiments are listed in Table 6.

The bioavailability of CBD nano lipospheres was significantly greater in comparison to CBD alone. Similar results were obtained for the Cmax values.

TABLE 6

PK parameters derived from PO administration of CBD and CBD nano lipospheres 15 mg/kg (n = 6 for each group).

| AUC (min*ng/mL) | $C_{max}$ (ng/mL) | |
| --- | --- | --- |
| 15533 ± 11679 | 105 ± 103 | CBD |
| 46356 ± 14567 (*) | 337 ± 100 (*) | CBD nano-lipospheres |

(*) Significant difference (p < 0.05) from CBD corresponding value is found

Figure 4:
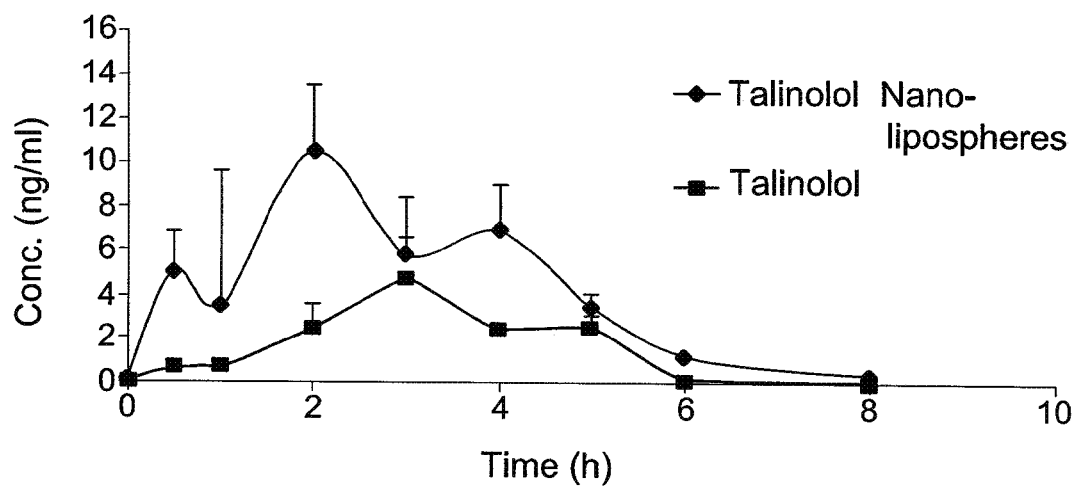
FIG. 4 presents plasma talinolol concentration-time plot (mean±S.E.M.) following per os (PO) administration 4 mg/kg of talinolol vs. AM-nano-liposheres (n=5 for each group).

Thus, incorporation of CBD into nano lipospheres is a promising strategy to overcome major obstacles in the way of development oral treatments with CBD such as first pass hepatic metabolism, instability in the acidic gastric pH and/or low water solubility, leading to incomplete absorption Talinolol PK Results Significantly higher plasma talinolol concentrations were obtained following talinolol nano lipospheres administration in comparison to free talinolol (FIG. 4). Corresponding increase in AUC and $C_{max}$ values are shown in Table 7.

TABLE 7

Summary of PK parameters derived from PO administration of talinolol vs. talinolol nano-liposheres at the dose of 4 mg/kg (n = 5 for each group).

| Talinolol | Talinolol nano-lipospheres | |
| --- | --- | --- |
| 11.9 ± 2.71 (*) | 35.98 ± 8.09 | AUC (Hr*ng/mL) |
| 5.55 ± 1.65 | 15.28 ± 4.7 | $C_{max}$ (ng/mL) |
| 1.15 ± 0.19 | 1.31 ± 0.23 | $T_{1/2}$ (hr) |

Based on this finding we conclude that nano-lipospheres possess the ability to inhibit intestinal P-gp efflux and thus to increase the oral bioavailability of intra enterocyte P-gp efflux substrates upon oral administration.

AM Tissue Distribution Studies

The rats were randomly assigned into two groups (n=3 in each group) and received AM or AM nano-lipospheres (12.5 mg/kg) for 5 days, once daily by oral gavage. Two hours after the last dose the rats were euthanized by $CO_2$ and liver and heart were removed and weighted. Plasma samples were collected as well.

Figure 5:
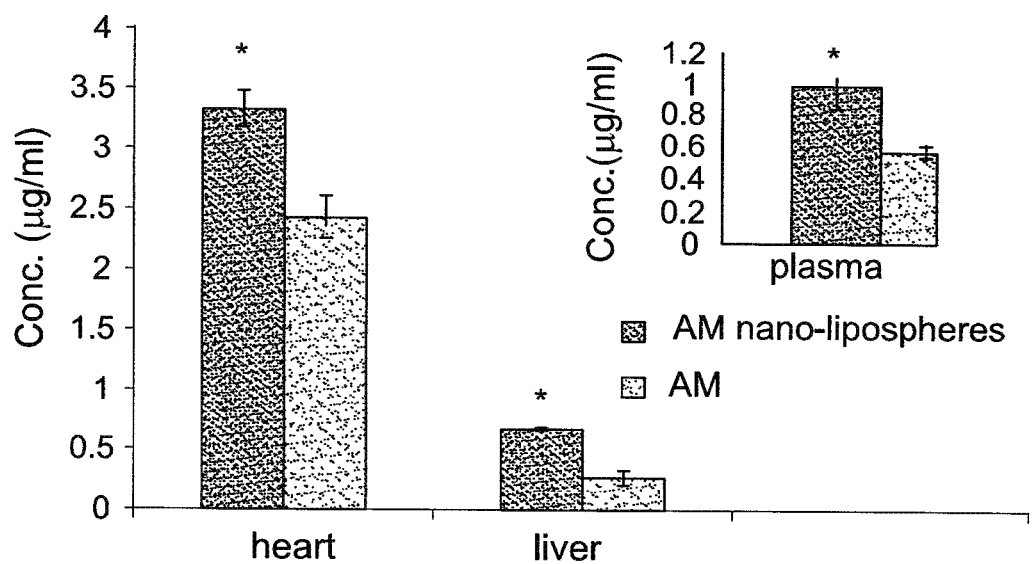
FIG. 5 presents plasma (m/mL) and tissue (m/g) concentrations of AM following PO administration of 12.5 mg/kg of AM and AM nano-liposheres for 5 days. Significant difference was found both in plasma and in corresponding heart and liver concentrations. (n=3 for each group).
Figure 6A:
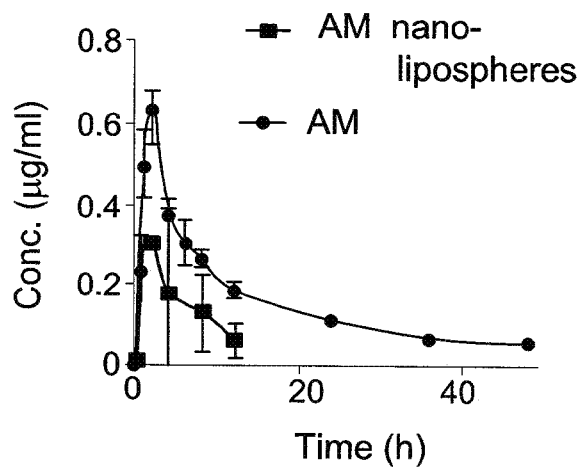
FIGS. 6A-D present plasma AM concentration-time plot (mean±S.E.M.) following PO administration 12.5 mg/kg of AM vs. AM-nano-liposheres (A), AM vs. AM+blank nano-liposheres (B), AM-nano-liposheres vs. AM+blank nano-liposheres (C), and AM-nano-liposheres vs. AM-nano-liposheres+blank nano-liposheres in the dose of 12.5 mg/kg (D). (n=6 for each group).
Figure 6B:
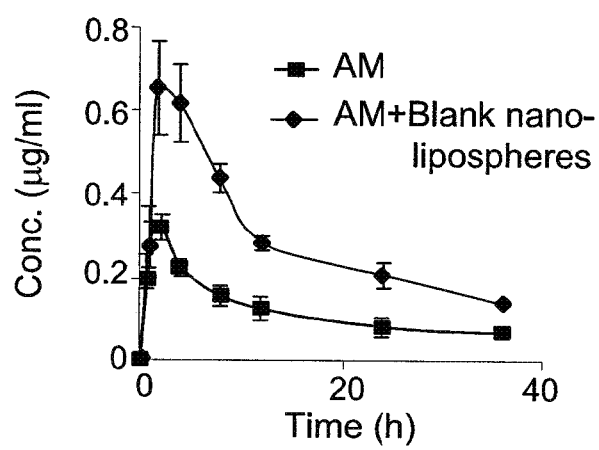
Figure 6C:
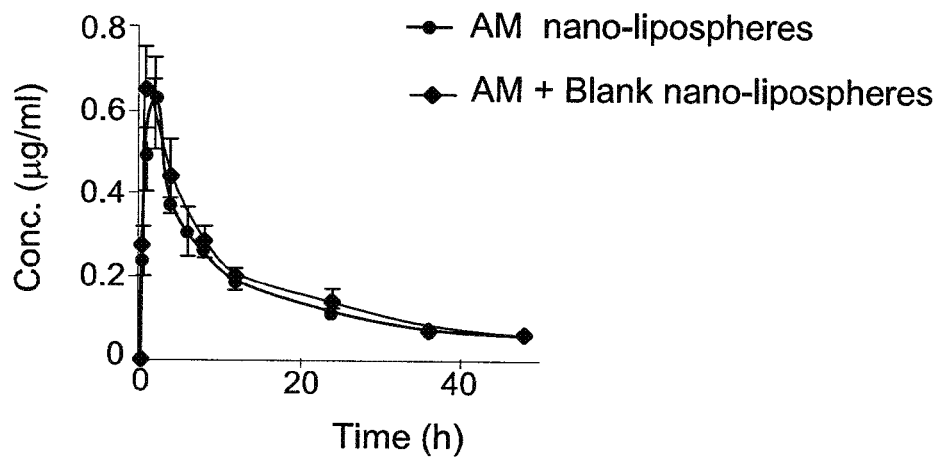
Figure 6D:
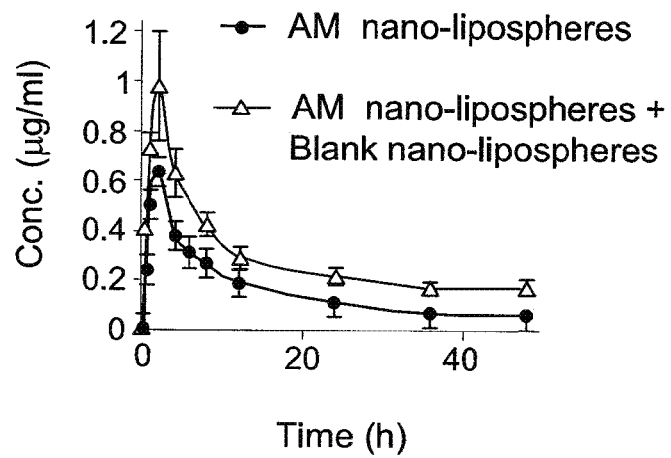

The tissue distribution results (FIG. 5) corroborate the increased plasma AUC obtained following single AM nano-lipospheres administration. Following chronic oral administration of AM nano-lipospheres and AM, we observed increased tissue (heart and liver) and corresponding plasma concentrations of AM in the AM nanolipospheres group. Interestingly, the extent of increase was similar in both tissues and plasma (about 1.5 folds). Since AM has a high volume of distribution and is extensively bound to tissues, the correlation between single and multiple dosing results emphasizes that the enhanced bioavailability of AM nano-lipospheres is a constant and profound effect.

Blank Nano Lipospheres Co-Administration Studies

For the assessment of blank nano-lipospheres co-administration effect on AM bioavailability, blank nano-lipospheres not containing AM were freshly prepared as described above and administered by oral gavage. AM (Amiodacore®) was administered immediately after that by the same route (n=6). The blank nanolipospheres volume was equal to AM nano-lipospheres volume administered in the bioavailability studies and the AM dose was 12.5 mg/kg (approximately 150 μl of 25 mg/mL AM solution).

For assessment of blank nano-lipospheres co-administration effect on AM nano-lipospheres bioavailability, AM nano-lipospheres were prepared as described above and administered by oral gavage. The administered dose was 12.5 mg/kg (n=6). Blank nano-lipospheres were freshly prepared and 1 mL was administered by the same route. Systemic blood samples (0.35 mL) were taken at 5 min pre-dose, 0.5, 1 2, 4, 8, 12, 24, 36 and 48 h post-dose. To prevent dehydration equal volumes of physiological solution were administered to the rats following each withdrawal of blood sample. Plasma was separated by centrifugation (4000 g, 7 min, 4° C.) and stored at −20° C. pending analysis (FIGS. 6A-D).

Blank Nano Lipospheres Co-Administration Results

The bioavailability of AM nano-lipospheres, AM+blank nano-lipospheres, and AM nano-lipospheres+blank nano-lipospheres was significantly greater in comparison to AM alone. Similar results were obtained for the Cmax values. Moreover, the AUC value following AM nano-lipospheres+ blank nano-lipospheres administration was significantly higher than other delivery systems. There was no significant difference found between the obtained AUC and Cmax values following AM nano-lipospheres and AM+blank nano-lipospheres administration. These results demonstrate that co-administration of blank nano-lipospheres with the drug has the same effect on its bioavailability as the incorporation into the nano-lipospheres.

TABLE 8

Summary of PK parameters derived from PO administration of AM, AM nano-lipospheres, AM + blank nano-lipospheres and AM- nano-lipospheres + blank nano-lipospheres in the dose of 12.5 mg/kg (n = 5 for each group).

| | AM | AM nano-lipospheres | AM nano-lipospheres + blank nano-lipospheres | AM + blank nano-lipospheres |
| --- | --- | --- | --- | --- |
| AUC (hr*μg/ml) | 4.54 ± 2.6 | 9.52 ± 0.47 (*) | 13.0 ± 4.78 (*†) | 10.65 ± 4.38 (*) |
| Cmax (μg/mL) | 0.36 ± 0.07 | 0.66 ± 0.08 | 1.32 ± 0.54 (*†) | 0.73 ± 0.16 (*) |
| T½ (hr) | 11.3 ± 4.26 | 18.0 ± 5.41 | 16.6 ± 6.36 | 12.3 ± 2.21 |
| V/F (mL/kg) | 34320 ± 5447 | 33774 ± 8638 | 24421 ± 8099 | 22451 ± 4950 |

TABLE 8-continued

Summary of PK parameters derived from PO administration of AM, AM nano-liposheres, AM + blank nano-liposheres and AM- nano-liposheres + blank nano-liposheres in the dose of 12.5 mg/kg (n = 5 for each group).

|  | AM | AM nano-lipospheres | AM nano-liposheres + blank nano-lipospheres | AM + blank nano-lipospheres |
|---|---|---|---|---|
| CL/F (mL/hr/kg) | 2412 ± 1428 | 1315 ± 66.3 | 1061 ± 396 | 1309 ± 454 |
| F (%) | 23.66 | 49.60 (*) | 67.96 (*) | 55.50 (*) |

(*) Significant difference (p < 0.05) from amiodarone corresponding value is found.
(†) Significant difference (p < 0.05) from (amiodarone + blank nano-liposheres) and (nano-liposheres + Blank nano-liposheres) corresponding value is found Absolute bioavailability (F) values were calculated using the following equation $$F = \frac{AUC_{iv} * Dose_{po}}{AUC_{po} * Dose_{iv}}$$

and utilizing the AM $AUC_{iv}$ values from our preliminary IV studies.

In addition, the absolute CL values were back calculated by multiplying the CL/F obtained for each group by its corresponding F value calculated as described above. No significant difference was found between the CL values of the different study groups and the CLiv value from our preliminary study, implying that nano-liposheres administration did not affect AM clearance rate and extent.

Investigation of Duration of Nano-Liposheres Effect on GI Absorption and Enterocyte Recovery Freshly prepared as described above blank nano-lipospheres were administered by oral gavage. The blank nano-lipospheres volume was equal to AM nano-liposheres volume administered in the bioavailability studies. After 2 hours 12.5 mg/kg AM solution prepared from Amiodacore® ampoules content as described above was administered (n=3). The control group received 12.5 mg/kg AM solution prepared from Amiodacore® ampoules at the same time point (n=3). In the investigation of duration of nano-lipospheres effect on GI absorption of AM, the last sampling point was 12 hours, assuming the effect will not last beyond this stage.

Figure 7:
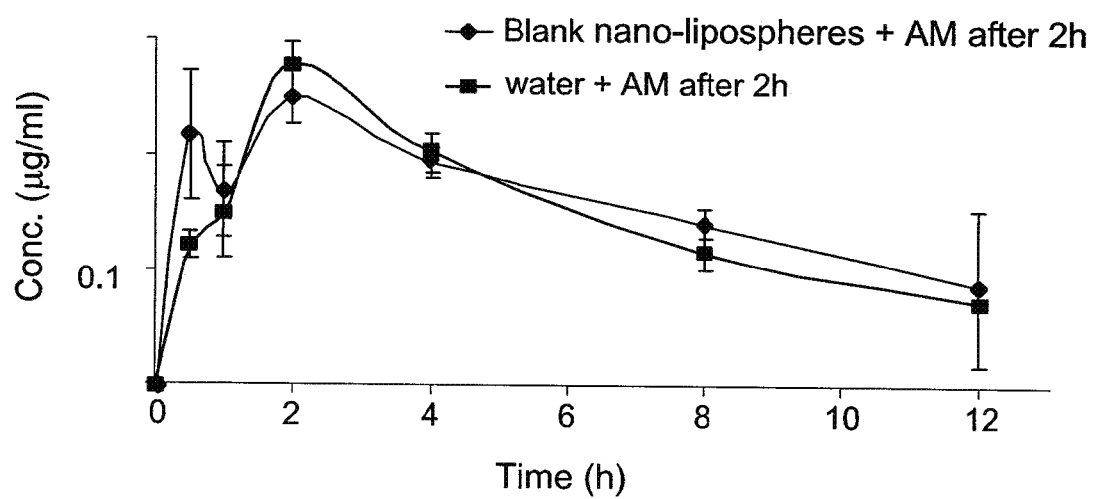
FIG. 7 presents plasma AM concentration-time plot (mean±S.E.M.) following PO administration of blank nano-liposheres following AM (12.5 mg/kg) administration after 2 h or water following AM (12.5 mg/kg) administration after 2 h (n=3 for each group).

Duration of Nano-Liposheres Effect on GI Absorption and Enterocyte Recovery Results The plasma concentration time profiles for AM following oral administration at a dose of 12.5 mg/kg 2 hours after administration of blank nano-liposheres or water are shown in FIG. 7. There was no significant difference in the obtained AM plasma concentrations between the groups. These results suggest that the effect of nano-liposheres on AM bioavailability is reversible and lasts no more than 2 hours.

AM Pharmacodynamic (PD) Study

Most of the investigations described so far have evaluated the pharmacokinetics of the drug when incorporated in lipospheres and very few investigations have demonstrated pharmacodynamic efficacy. Although pharmacokinetic studies are sufficient to establish proof of concept for lipospheres, the results of the pharmacokinetic study should preferably be corroborated by pharmacodynamic studies. This is particularly important for drugs which do not show pharmacokinetic-pharmacodynamic correlation. Such aspects should be carefully considered while planning investigations on the lipospheres.

Bradicardia and hypotension have been reported as the most common haemodynamic effects caused by acute AM administration. Several studies assessed the effect of AM on heart rate in freely moving rats using radiotelemetry method following IV and PO AM administration. Radiotelemetry is the "state of the art" for monitoring physiological functions in awake and freely moving animals, while minimizing stress artifacts and effects of anesthesia.

Da Silva et al. (*Am J Physiol Regul Integr Comp Physiol.,* 283(2):R543-8m 2002) reported a significant increase in R-R interval 5 min post AM IV administration (50 mg/kg). Such bradicardia, observed in several studies following single high IV AM dose can be attributed to several mechanisms; for instance, $Na^+$ and $Ca^{2+}$ channel blocking actions depressing the automaticity of sinus node, a non-competitive beta-adrenoreceptor blockade, a reserpine like sympatholytic action and direct $K^+$ channel blockade. In contrast, a lower AM dose (25 mg/kg) triggered a brief tachycardia, indicating that only higher AM dose was able to counteract the baroreflex allowing the reflex tachycardia to occur.

The deferential effect of AM on heart rate was used as a pharmacodynamic marker for assessment of AM pharmacological effect following oral administration.

Transmitter Implantation

Male Wistar rats (Harlan, Israel) weighing 300-350 g were kept under a 12 h light/dark cycle with free access to water and food (standard rat chow) Animals were anesthetized for the period of surgery by intraperitoneal injection of 1 mL/kg of ketamine-xylazine solution (90/10%, respectively).

An ECG transmitter (TA11CA-F40, Data Sciences International Inc., St. Paul, MN) was implanted subcutaneously over the scapula with the leads in a Lead 2 configuration by tunneling subcutaneously from the dorsal incision using a trocar. The negative lead was placed in the area of the right shoulder and the positive lead was placed immediately to the left of the xyphoid space and caudal to the rib cage.

After the surgery the animals were left to recover for 5 days. During the first 72 hours of the recovery period the animals were treated with Bitryl (5 mg/kg) and Tramadol (5 mg/kg).

Data Recording and Analysis

A night before the recording the animals were relocated in their cages to the recording room in order to adjust to the new environment. The experiment started after the animals were at least 8 hours with food deprivation.

The signal from the transmitters was received by two RLA 2000 receivers and transmitted via a Data Exchange Matrix to a Dataquest PCI card. The data were recorded continuously during the whole experiment at 1000 Hz rate with no filter cutoff and full scale at 10 mV.

The collected data were interpreted by Dataquest A.R.T program. The IBI (R-R duration, sec) and HR (bpm) were calculated in average values of each 10 min of the recording.

At the beginning the baseline were recorded at least for 120 min. After establishing stable recording the rats were treated by oral gavage. During the treatment the data was collected and afterwards extracted in further analysis.

Dosing Protocol

Two groups of three rats received the treatment in a cross over manner, meaning each rat received each treatment once. The treatments were as follows:

AM: 12.5 mg/kg AM solution prepared from Amiodacore® ampoules content (AM 50 mg/mL) dissolved in water to obtain 2.5 mg/mL concentration AM Nano-Lipospheres:

AM containing nano-lipospheres were freshly prepared 30 min before each experiment, by vortex-mixing of the pro nano-dispersion containing AM in water (1:9) pre-heated to 37° C. for 30 sec. The obtained AM concentration was 3 mg/mL. The AM nano-lipospheres (12.5 mg/kg) were administered to the animals by oral gavage.

After each recording phase the rats were left for the washout period of 7 days before the next recording phase.

AM+Blank Lipospheres:

Blank nano-lipospheres not containing AM was freshly prepared as described above and was administered by oral gavage. AM (Amiodacore®) was administered immediately after that by the same route. The blank nano-lipospheres volume was equal to AM nano-lipospheres volume administered in to the AM group and the dose was 12.5 mg/kg identical.

Blank Nano-Lipospheres with AM Nano-Lipospheres:

AM-nano-lipospheres were prepared as described above and was administered by oral gavage. The administered dose was 12.5 mg/kg. Blank nano-lipospheres were freshly prepared and 1 mL was administered by the same route.

Sham Group received equivalent volume of nano-liposphere without any active ingredient.

After each recording phase the rats were left for the washout period of 7 days before the next recording phase.

Pharmocodynamic Results

One week following transmitter implantation all animals did not exhibit significant changes of body weight as compared to the pre-surgery status. A normal behavioral pattern was observed 48-72 hours after the surgery, including circadian rhythm, grooming, exploration of the cage and reactivity to handling.

Initially, baseline recording were performed in order to obtain the signal pattern and to assure that the ECG leads were stable at their insertion points. ECG signals were not filtered or smoothed neither during the recording session nor during analysis. All of the animals showed fine signal strength and ECG wave pattern. The recording yielded adequate R wave amplitudes and QRS complexes for determinations of heart rate (HR) and intra-beat R-R interval (IBI) variability.

In order to inspect separately the effect of each delivery method, we first calculated the mean baseline IBI duration throughout 60 min prior the administration. The drug was administered at t=60 min Post administration the data was calculated throughout 180 min. The net change was calculated as the percentage of the change for each drug administration mode relative to the baseline recording. The changes from base-line in two parameters: IBI and HR were analyzed in two points: 90 min. post administration (mid phase) and 180 min post administration (end phase) (Tables 9A-B and 10A-B, respectively).

Sham operated group that received only the blank nano-lipospheres without any active compound, didn't exhibit any significant change in the IBI duration and HR.

Following AM (12.5 mg/kg) administration, the mean IBI values decreased from 0.175±0.006 sec to 0.143±0.0074 sec and the heart change increased 344±13.58 BPM to 452.916±20.01 as expected.

Figure 8:
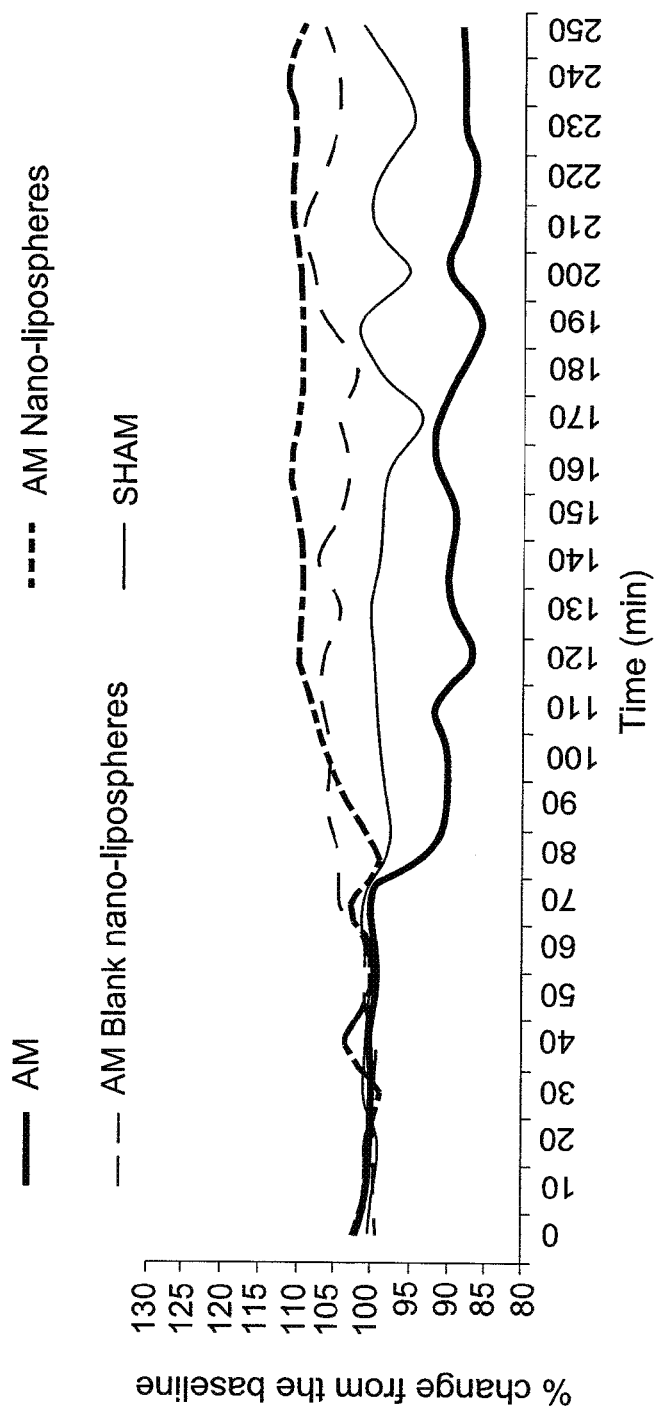
FIG. 8 presents mean IBI changes (as percentage from baseline) following 12.5 mg/kg AM administration in 3 different formulations: AM, AM nano-liposheres, AM+Blank nano liposheres and administration of blank nano-liposheres. The drug was administered at t=60 min (n=6 for each group)
Figure 9:
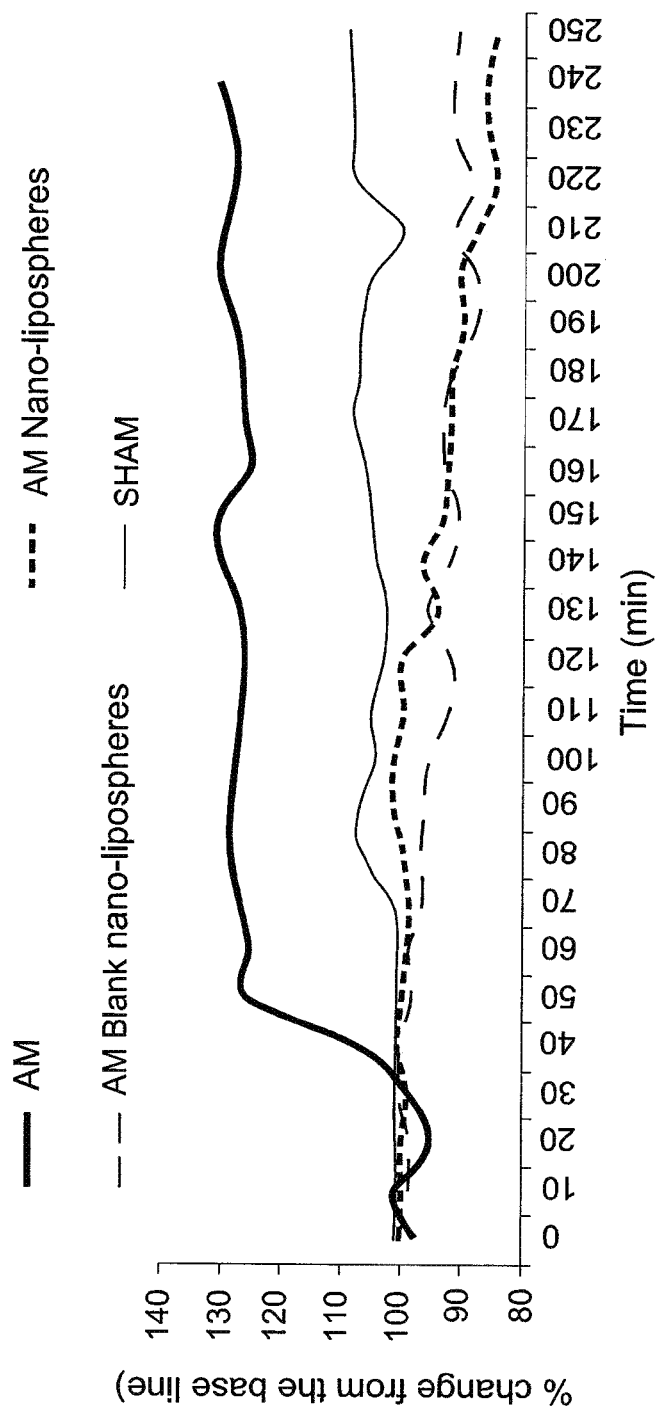
FIG. 9 presents mean HR changes (as percentage from baseline) following 12.5 mg/kg AM administration in 3 different formulations: AM, AM nano-liposheres, AM+Blank nano liposheres and administration of blank nano-liposheres. The drug was administered at t=60 min (n=6 for each group).

When the drug was incorporated into the nano-liposplieres (AM nano-liposplieres) the mean IBI increased from 0.179±0.0026 sec to 0.197±0.009 sec and the heart rate decreased from 390.9±9.4 BPM to 365.334±7.089 BPM. Thus, at same when the drug at the same dosage was incorporated into the nano-liposplieres, a reverse effect was shown. This effect, bradycardia, of the drug is characteristic to the high dosage of AM meaning that the drug incorporation to the nano-liposplieres increases the bioavailability of the drug and the drug concentrations at the active site (cardiac tissue). Similar bradycardic effect was created when AM was co-administered with blank nano-liposplieres (AM+Blank nano-liposplieres): the mean IBI increased from 0.175±0.002 sec to 0.184±0.003 sec and the HR decreased from 377.54±4.82 BPM to 342.522±13.94 BPM (FIGS. 8 and 9).

TABLE 9

Mean HR (A) and IBI (B) changes (as percentage from baseline) following 12.5 mg/kg AM following administration in 3 different formulations: AM, AM nanoliposplieres (SNEDDS), AM + Blank nano liposplieres and administration of blank nanoliposplieres, as measured at the mid phase (90 min following oral administration)

| A. HEART RATE (BPM) | | | |
|---|---|---|---|
| CHANGE % | MID PHASE | BASELINE | |
| 131.28 | 452.916 ± 20.01 | 344 ± 13.58 | AM |
| 93.46 | 365.334 ± 7.089 | 390.9 ± 9.4 | AM SNEDDS |
| 90.73 | 342.522 ± 13.93 | 377.54 ± 4.82 | AM + BLANK SNEDDS |
| 105.72 | 354.605 ± 18.43 | 335.42 ± 12.89 | SHAM |
| HEART RATE (BPM) | | | |
| CHANGE % | END PHASE | BASELINE | |
| 128.43 | 443.071 ± 11.06 | 344 ± 13.58 | AM |
| 95.37 | 372.839 ± 11.54 | 390.9 ± 9.4 | AM SNEDDS |

TABLE 9-continued

Mean HR (A) and IBI (B) changes (as percentage from baseline) following 12.5 mg/kg AM following administration in 3 different formulations: AM, AM nanolipospheres (SNEDDS), AM + Blank nano lipospheres and administration of blank nanolipospheres, as measured at the mid phase (90 min following oral administration)

| | | | |
|---|---|---|---|
| 92.61 | 349.626 ± 8.00 | 377.54 ± 4.82 | AM + BLANK SNEDDS |
| 106.09 | 355.870 ± 11.63 | 335.42 ± 12.9 | SHAM |

B.
IBI (sec)

| CHANGE % | MID PHASE | BASELINE | |
|---|---|---|---|
| 88.86 | 0.1435 ± 0.008 | 0.175 ± 0.006 | AM |
| 110.01 | 0.197 ± 0.009 | 0.179 ± 0.0026 | AM SNEDDS |
| 104.04 | 0.182 ± 0.003 | 0.175 ± 0.002 | AM + BLANK SNEDDS |
| 98.57 | 0.173 ± 0.01 | 0.175 ± 0.001 | SHAM |

IBI (sec)

| CHANGE % | END PHASE | BASELINE | |
|---|---|---|---|
| 89.79 | 0.143 ± 0.007 | 0.175 ± 0.006 | AM |
| 108.76 | 0.195 ± 0.008 | 0.179 ± 0.0026 | AM SNEDDS |
| 105.39 | 0.184 ± 0.003 | 0.175 ± 0.002 | AM + BLANK SNEDDS |
| 98.39 | 0.172 ± 0.01 | 0.175 ± 0.001 | SHAM |

TABLE 10

Mean HR (A) IBI (B) and changes (as percentage from baseline) following 12.5 mg/kg AM following administration in 3 different formulations: AM, AM nanolipospheres, AM + Blank nano lipospheres and administration of blank nanolipospheres, as measured at the end phase (180 min following oral administration).

A.
HEART RATE (BPM)

| CHANGE % | MID PHASE | BASELINE | |
|---|---|---|---|
| 131.28 (*) | 452.916 ± 20.01 | 344 ± 13.58 | AM |
| 93.46 (*) | 365.334 ± 7.089 | 390.9 ± 9.4 | AM SNEDDS |
| 90.73 (*) | 342.522 ± 13.94 | 377.54 ± 4.82 | AM + BLANK SNEDDS |
| 105.72 | 354.605 ± 18.43 | 335.42 ± 12.89 | SHAM |

HEART RATE

| CHANGE % | END PHASE | BASELINE | |
|---|---|---|---|
| 128.43 (*) | 443.07 ± 11.06 | 344 ± 13.58 | AM |
| 95.37 (*) | 372.839 ± 11.54 | 390.9 ± 9.4 | AM SNEDDS |
| 9.61 (*) | 349.626 ± 8.00 | 377.54 ± 4.82 | AM + BLANK SNEDDS |
| 106.09 | 355.870 ± 11.63 | 335.42 ± 12.89 | SHAM |

B.
IBI (sec)

| CHANGE % | MID PHASE | BASELINE | |
|---|---|---|---|
| 88.86 (*) | 0.1435 ± 0.008 | 0.175 ± 0.006 | AM |
| 110.01 (*) | 0.197 ± 0.009 | 0.179 ± 0.0026 | AM SNEDDS |
| 104.04 (*) | 0.182 ± 0.003 | 0.175 ± 0.002 | AM + BLANK SNEDDS |
| 96.57 | 0.173 ± 0.01 | 0.175 ± 0.001 | SHAM |

IBI (sec)

| CHANGE % | END PHASE | BASELINE | |
|---|---|---|---|
| 89.79 (*) | 0.143 ± 0.007 | 0.175 ± 0.006 | AM |
| 108.76 (*) | 0.195 ± 0.008 | 0.179 ± 0.0026 | AM SNEDDS |
| 105.39 (*) | 0.184 ± 0.003 | 0.175 ± 0.002 | AM + BLANK SNEDDS |
| 98.39 | 0.172 ± 0.01 | 0.175 ± 0.001 | SHAM |

These findings demonstrate that Amiodarone bioavailability increases not only when it is encapsulated in nanolipospheres, but even the simultaneous presence of empty (i.e. drug-less) nano-lipospheres in the intestine. Moreover, encapsulation into nano-lipospheres reduces the high variability in plasma concentrations, typical for amiodarone and other BCS class 2 compounds. Our PD studies results corroborate the PK findings and demonstrate similar PD effect upon administration of AM nano-lipospheres and AM+blank nano-lipospheres, which is significantly different from the PD effect obtained upon administration of free AM.

Parenteral Administration of the Nano-Lipospheres

Figure 10:
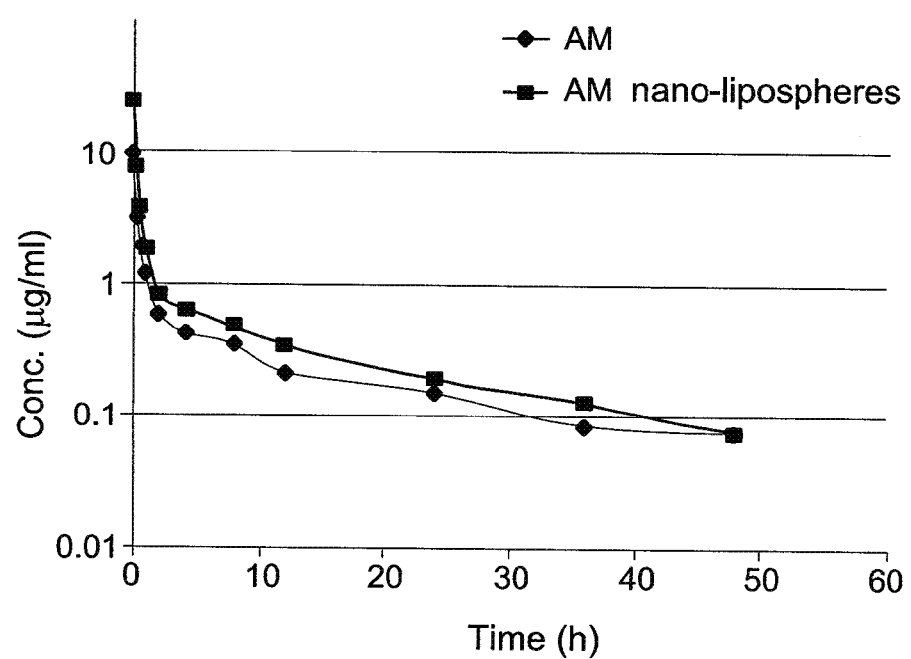
FIG. 10 presents plasma concentration-time profile (±SE) obtained following IV administration of 12.5 µg/kg Amiodacore® and AM nano-liospheres.

As for IV administration, the nano-liposphere formulation alters the biodistribution parameters of a given molecule, as well as its disposition. FIG. 10 demonstrates the plasma concentration-time profile obtained following IV administration of 12.5 µg/kg Amiodacore® and AM nano-lipospheres. It can be seen that the administration of nano-lipospheres resulted in higher plasma concentrations of AM at the central compartment during the first disposition phase. The AUCs were 22.1 and 17.1 µg/mL after AM nano-lipospheres and Amiodacore® administration respectively.

It can be seen that the nano-lipospheres also alter the PK parameters of the administered drug. Significant reduction in volume of distribution and in clearance of amiodarone when administered as nano-lipospheres are observed (Table 11). The reduction in Vss is a result of better solubility of the drug in plasma while encapsulated in nano-lipospheres. Thus, more drug is retained in the central compartment. As drug encapsulated in the formulation reaches P-gp containing barriers (such as the blood-brain barrier), it might possess improved penetration qualities due to the P-gp inhibition ability of the formulation. As a result, penetration of parenteral drugs to P-gp expressing tissues will be improved.

TABLE 11

PK parameters obtained following IV administration of 12.5 µg/kg Amiodacore ® and AM nano-lipospheres.

| Cl (mL/hr/kg) | Vss (mL/kg) | AUC (hr*ug/mL) | HL(h) | |
|---|---|---|---|---|
| 549 | 8002 | 22.9 | 17.1 | nano-lipospheres |
| 818 | 18138 | 15.3 | 22.1 | Amiodacore |

In-Vitro Mechanistic Investigation
In Vitro Permeability Studies Using Caco-2 Cells:

Caco-2 cell line is a broadly used in vitro model to study various aspects of intestinal permeability of drug molecules, which was established by Fogh in 1974. The Caco-2 cell line is derived from a human colon carcinoma. These cells spontaneously differentiate to enterocytes under conventional cell culture conditions. Caco-2 cells exhibit morphological as well as biochemical similarities to intestinal (absorptive) enterocytes. The cells form tight intercellular junctions and microvilli, express several transporters (e. g. sugar carrier, bile acid carrier, large neutral amino acid carrier, and P-gp) and metabolic enzymes (e g aminopeptidases, esterases, sulfatases, and cytochrome P450 enzymes). The unusually high degree of differentiation, morphological and functional structure resembling enterocytes has resulted in Caco-2 becoming one of the most popular cell culture models to study intestinal epithelial integrity and drug transport.

For determination of nano-lipospheres ability to inhibit intestinal P-gp efflux pumps, Caco-2 transport study was performed using talinolol as a model molecule. As previously stated, talinolol is a known P-gp substrate and is not metabolized by the intra-enterocyte CYP enzymes. In this case, the donor compartment of the transwells contained either 10 µg/mL talinolol, or 10 µg/mL talinolol with blank nanolipospheres (amount equivalent to 100 µg/mL AM-nano lipospheres). At fixed time points (0, 30, 60, 90, 120, and 150 min), 150 µL samples were withdrawn from the receiver side, and similar volumes of blank buffer were added to maintain constant volume. C14-Mannitol, a commonly used marker for passive paracellular permeability, was used for further evaluation of proper carrying out of each study.

Figure 11:
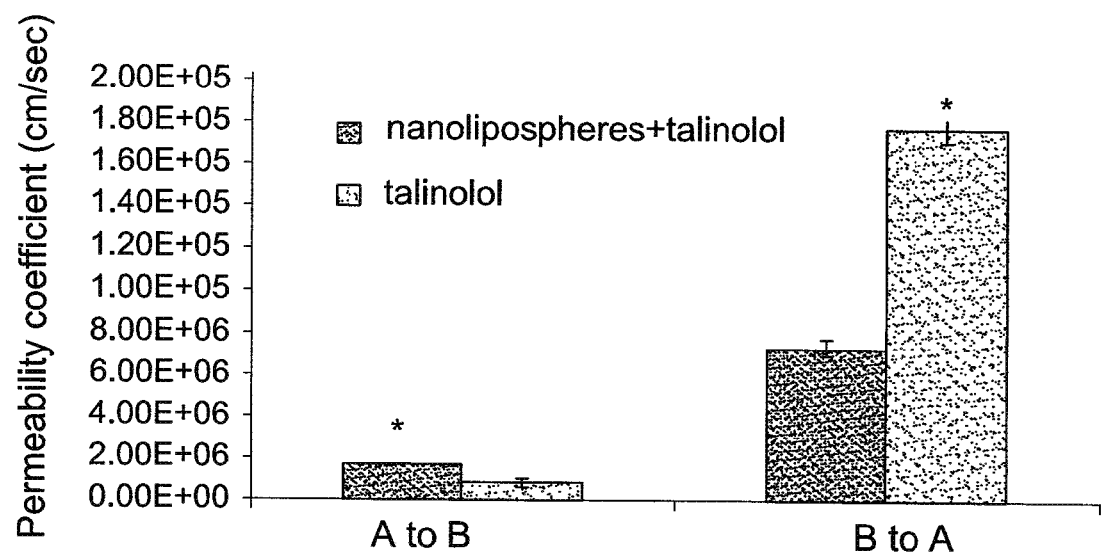
FIG. 11 presents papp (±SEM) values of talinolol vs. talinolol+blank nano-liospheres in Caco-2 model in A to B and B to A directions (n=3 for each group). Significantly higher (p<0.001) Papp values of talinolol+blank nano-liospheres vs. talinolol were obtained in A to B direction. Significant (p<0.001) reduction in Papp values obtained for talinolol+blank nano-liospheres vs. talinolol in B to A direction.

In-vitro permeability studies of talinolol through Caco-2 monolayers resulted in significantly higher ($p<0.001$) permeability coefficient values of talinolol+blank nano-lipospheres vs. talinolol ($1.73 \times 10^{-6}$ and $7.66 \times 10^{-7}$ respectively) in A to B direction. As expected for P-gp substrate, both talinolol and talinolol+blank nano-lipospheres Papp values obtained in the B to A direction are higher than the corresponding Papp values obtained in the A to B direction. B to A permeability resulted in statistically significant ($p<0.001$) reduction in Papp values obtained for talinolol+blank nano-lipospheres vs. talinolol ($7.36 \times 10^{-6}$ and $1.77 \times 10^{-5}$ respectively), as expected for P-gp substrate when P-gp activity is inhibited (FIG. 11).

It should be emphasized that talinolol was not incorporated into nano-lipospheres, but administered simultaneously. These results suggest that nano-lipospheres possess the ability to inhibit P-gp efflux and thus to increase the oral bioavailability of compounds subjected to extensive intra-enterocyte efflux. Furthermore, nano-lipospheres can inhibit P-gp not only by incorporation of the compound into this delivery system but also when nano-lipospheres e.g. blank nano-lipospheres are administered simultaneously with the active compound. As expected for a P-gp substrate, both values obtained in the basal-to-apical direction are higher than the Papp obtained in the apical-to-basal direction. Interestingly, basal-to-apical permeability resulted in significant reduction in Papp values obtained for talinolol-nano lipospheres vs. talinolol. This pattern is typical for P-gp substrates in the presence of a P-gp inhibitor; while apical-to-basal efflux is increased due to P-gp inhibition, the opposite direction transport is decreased as a result of reduced P-gp contribution to drug transport from the enterocyte to the lumen.

Figure 12:
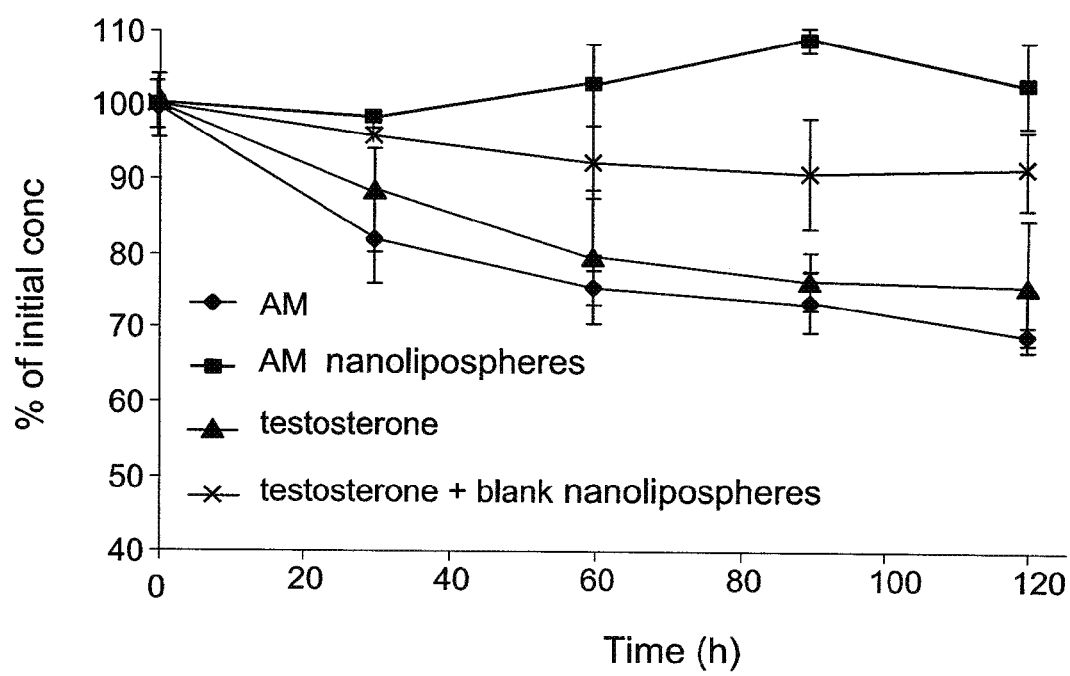
FIG. 12 presents the difference (p<0.01) found between intact AM concentrations remaining following 120 min. incubation of AM nano-liospheres vs. AM in isolated rat CYP3A4 microsomes. Significant difference (p<0.05) was found between testosterone with blank nano-liospheres vs. testosterone alone incubated under the same conditions (n=3 for each study).

To comprehend the effects of nano-lipospheres on intra-enterocyte metabolic activity, we tested its effect on CYP3A4 mediated AM and testosterone (control CYP 3A4 substrate) metabolism in isolated rat CYP 3A4 microsomes (FIG. 12). Significant difference ($p<0.01$) was found between intact AM concentrations remaining following 120 min. incubation of AM-nano-lipospheres vs. AM ($102.4 \pm 5.61\%$ and $68.57 \pm 1.17\%$ respectively). In order to distinguish between mechanistic protection of nano-lipospheres from enzymatic degradation and the effect of nano-lipospheres ingredients on enzymatic activity, blank nano-lipospheres were added to testosterone and incubated in microsomes. Significant difference ($p<0.05$) was found between testosterone with nano-lipospheres vs. testosterone alone incubated at the same conditions ($91.26 \pm 5.31\%$ and $75.39 \pm 8.82\%$ respectively).

These results imply that increased bioavailability achieved by nano-lipospheres partially results from reduced first pass intra-enterocyte metabolism. Moreover, similarly to our in vivo results, the incorporation of the drug into nano-lipospheres was not necessary to gain the effect of increased bioavailability or reduced first pass metabolism, and co-administration of the drug with the blank nano-lipospheres resulted in comparable effects.

Safety and Toxicity Studies
In-Vitro Paracellular Transport Studies:

Caco-2 cells permeability studies were performed with paracellular transport marker C14-Mannitol (2 µCi/mL).

Samples (200 μL) were withdrawn from the basolateral side at the same fixed time points described above, and similar volumes of blank buffer were added following each withdrawal.

Transepithelial Electrical Resistance (TEER) Studies:

Caco-2 cells were grown on 12-transwell plate and cultured for 21 days The apical buffer was replaced with 0.6 mL pre-warmed (37° C.) apical buffer containing blank nano-lipospheres (amount equivalent to 100 μg/mL AM-nano-lipospheres). In order to evaluate the effect of the nano-lipospheres on the paracellular transport across the cells (i.e. the extent to which the tight junctions are opened), TEER values were measured at the above time points and compared to the TEER values measured in control cells containing only buffer.

Figure 13:
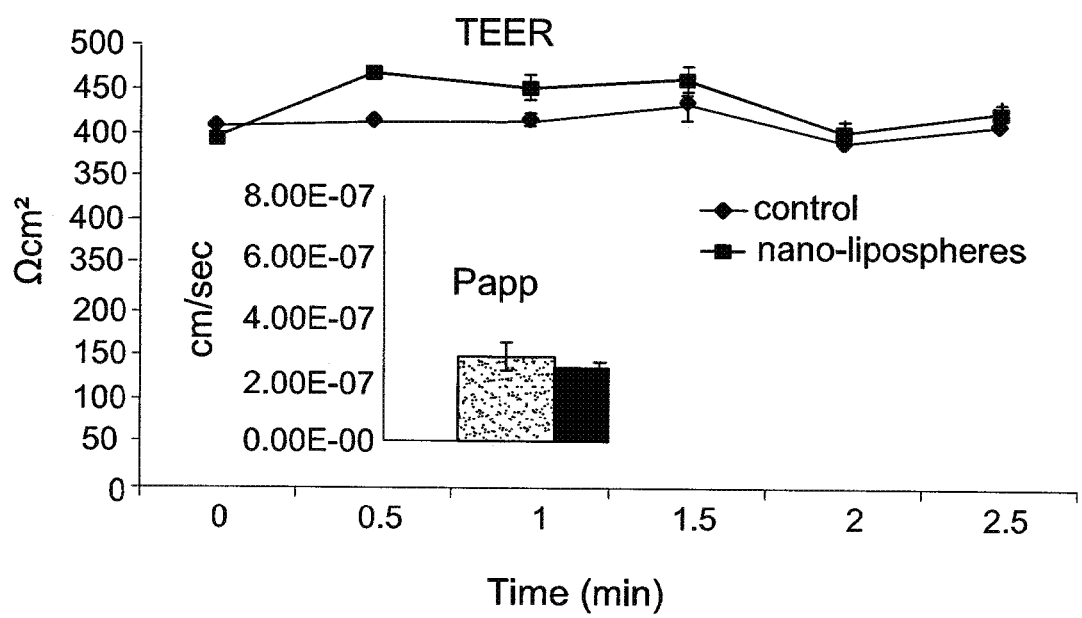
FIG. 13 presents TEER values (outer line chart) (±SD) of Caco-2 cells monolayers in the presence of blank nano-liospheres vs. buffer, which was used as a control (n=3). The embedded column chart represents Papp values (±SD) of mannitol across the Caco-2 monolayers in the presence of blank nano-liospheres vs. buffer.

In FIG. 13, the outer line represents the TEER values of Caco-2 monolayers in the presence of blank nano-lipospheres or control. There was no difference in the TEER values measured throughout the experiment both in the presence and absence of blank nano-lipospheres (p=0.19), indicating that the integrity of the monolayer was remained. The embedded chart represents the Papp values of mannitol (a paracellular transport marker) following incubation with blank nano-lipospheres or control in Caco-2 model. There was no significant difference in the permeability of mannitol in the presence of blank nano-lipospheres compared to buffer (p=0.51). These observations indicate that nano-lipospheres neither affect paracellular permeability, nor disrupt the enterocyte monolayer integrity.

Cellular Toxicity Studies:

Lactate dehydrogenase (LDH) is a cytoplasmic enzyme which is released into the culture supernatant when the plasma membrane is damaged. Nano-lipospheres toxicity was assessed over a range of concentrations (0.1, 1, 5, and 10% in medium) in Coco-2 cells grown as described above using LDH cytotoxicity detection kit, after the incubation of the cell culture with blank nano-lipospheres containing medium for 2 h. Percent of cell damage is calculated so that low control was the spontaneous LDH release measured in untreated cells medium and high control was 100% LDH release measured in cells incubated with 1% Triton X-100 containing medium.

Figure 14:
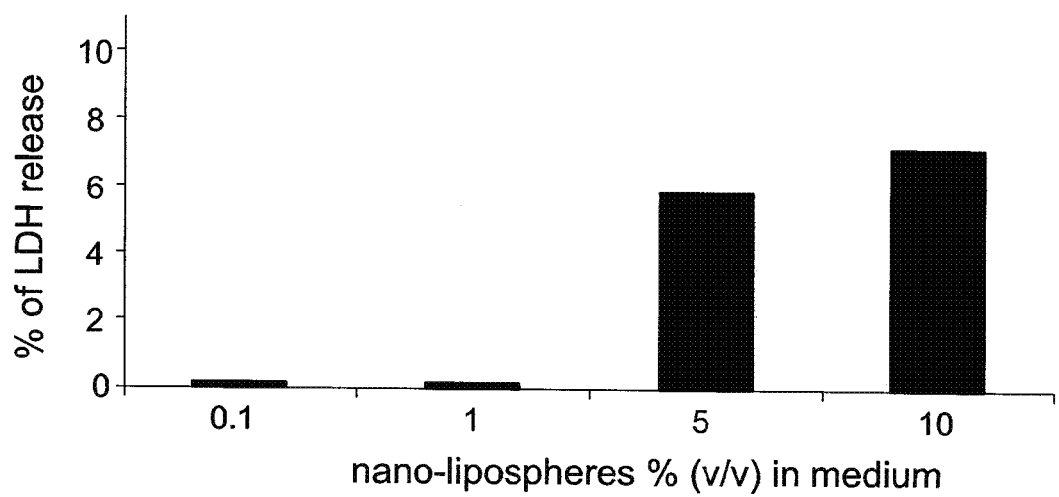
FIG. 14 presents the percent of LDH release (relatively to 100% release control) upon incubation of Caco-2 cell with medium containing various concentrations of blank nano-liospheres. Nano-liospheres increased LDH release in concentration dependant manner with highest toxicity obtained at 10% nano-liospheres concentration and negligible toxicity produce by nano-liospheres concentration of 1% and less.

As shown in FIG. 14, nano-lipospheres increased LDH release in concentration dependant manner with highest toxicity obtained at 10% nano-lipospheres concentration (7.27%) and negligible toxicity (<1%) produce by nano-lipospheres concentration of 1% and less compared to 100% toxicity standard. These results suggest that no significant damage is caused to the apical cell membrane of the enterocyte by nano-lipospheres administration. Moreover, an overestimation of cytotoxicity might be obtained in Caco-2 model since it is lacking the repair and recovery mechanisms present in the intact tissue.

Thus, it is shown that nano-lipospheres improve oral bioavailability of Class II compounds by multi-processes mechanism: increased GI milieu solubilization, reduced intra-enterocyte metabolism and reduced P-gp efflux activity. In addition to increased bioavailability, nano-lipospheres reduces the high variability typical for Class II compounds. Nano-lipospheres do not cause tissue or cell membrane damage. Therefore, the present invention further concerns a composition being the nano-lipo formulation as described above, but devoid of a drug ('empty composition) for oral administration for increasing the absorption of a drug with low bioavailability due to first pass intestinal metabolism or substrate of intestinal efflux transporters (e.g. P-gp) administered simultaneously, or in a close time window to the nano lipo formulation.

Based on these finding it is concluded that the nano-formulation serve as a platform for administration of drugs which are P-gp and CYP3A4 substrates that are characterized by low oral bioavailability and erratic absorption. Examples of P-gp and CYP3A4 substrates that are suitable candidates for administration in nanolipospheres are listed in Table 12.

TABLE 12

Examples of P-gp and CYP3A4 substrates at the gut-wall and the liver, which are suitable candidates for administration in nano-lipospheres

| | |
|---|---|
| Amlodipine | Calcium channel blockers |
| Diltiazem | |
| Felodipine | |
| Nicardipine | |
| Nifedipine | |
| Nimodipine | |
| Nisoldipine | |
| Verapamil | |
| Cyclosporine when administered with "empty" lipo-nanosphere formulation | Immunosuppressants |
| Sirolimus | |
| Tacrolimus | |
| Atorvastatin | Statins |
| Lovastatin | |
| Simvastatin | |
| Fexofenadine | Antihustamins |
| Buspirone | CNS drugs |
| Carbamazepine | |
| Pimozide | |
| Midazolam | |
| Triazolam | |
| Albendazole | Anti-fungal/antibiotics |
| Itraconazole | |
| Erythromycin | |
| Amiodarone | Miscellaneous |
| Cisapride | |
| Colchicine | |
| Sildenafil | |

Moreover, nano lipospheres of the present invention affect intestinal CYP3A4 enzyme in a reversible and non selective manner, such that it is possible that the nano lipospheres of the present invention inhibit other metabolic enzymes in the intestine e.g. CYP2C19 and CYP2C9.

Cannabidiol and Cannabidiol-Piperine Nano-Liposphere Formation (CBD-PNL and CBDpiperine-PNL, Respectively)

CBD nano lipospheres formulation was prepared by pre-concentrate preparation method. The final nano-lipospheres composition was based on preliminary formulation optimization studies and selected according to optimal solubilization capacity of the active ingredient. Initially amphiphilic co-solvent (ethyl lactate) and phospholipid (lecithin) at the ratio of 8:1, respectively were placed in a clean scintillation tube and heated to 40° C. until the lecithin was completely dissolved. Then triglyceride (tricaprin), polyoxyl 40-hydroxy castor oil, Tween 20, and Span 80 at the ratio of 1:1:1:1 were added; the mixture was gently stirred and heated to 40° C. till homogenous solution was formed. Further, CBD powder was added, forming the CBD preconcentrate containing 3% CBD. This pre-concentrate was gently stirred and heated to 40° C. till homogenous solution was formed. Upon gentle agitation in aqueous phase, this pre-concentrate spontaneously forms drug encapsulated nano-dispersion. For the preparation of CBD-Piperine-PNL piperine powder was added with CBD powder to form the CBD-Piperine-PNL. CBD solution in Propylen Glycol/ EthOH/Water 30/30/40 respectively was used as control throughout all in-vivo studies.

In-Vivo PK Studies

Animals: Male Wistar rats weighing 300-350 g were used for the in vivo studies. The project adhered to the principles of Laboratory Animal Care (NIH publication no. 85-23, revised 1985). All animals were deprived of food but not water 12 h prior to the experiments. All surgical and experimental procedures were reviewed and approved by the Animal Experimentation Ethics Committee of the Hebrew University Hadassah Medical School Jerusalem. An indwelling cannula was placed in the right jugular vein of each animal for systemic blood sampling.

CBD Relative Oral Bioavailability Studies, nano liposheres was freshly prepared 30 min before each experiment, by vortex-mixing of the pre-concentrate (CBD-PNL and CBD-Piperine-PNL) in water (1:9) pre-heated to 37 C0 for 30 sec. The obtained CBD and piperine concentrations were 3 mg/mL and 2 mg/ml, respectively. CBD-Piperine-PNL (15 mg/kg of CBD and 10 mg/kg of piperine) was administered to the animals by oral gavage (n=6). The control groups received (15 mg/kg) CBD solution in propylene glycol/EthOH/water 30/30/40 respectively (1 mg/mL) (n=6) or CBD-PNL ((15 mg/kg of CBD).

Systemic blood samples (0.35 mL) were taken at 5 min pre-dose, 20 min, 40 min, 1 h 1.3 h, 1.6 h, 2 h, 3 h and 4 h post-dose.

Figure 15:
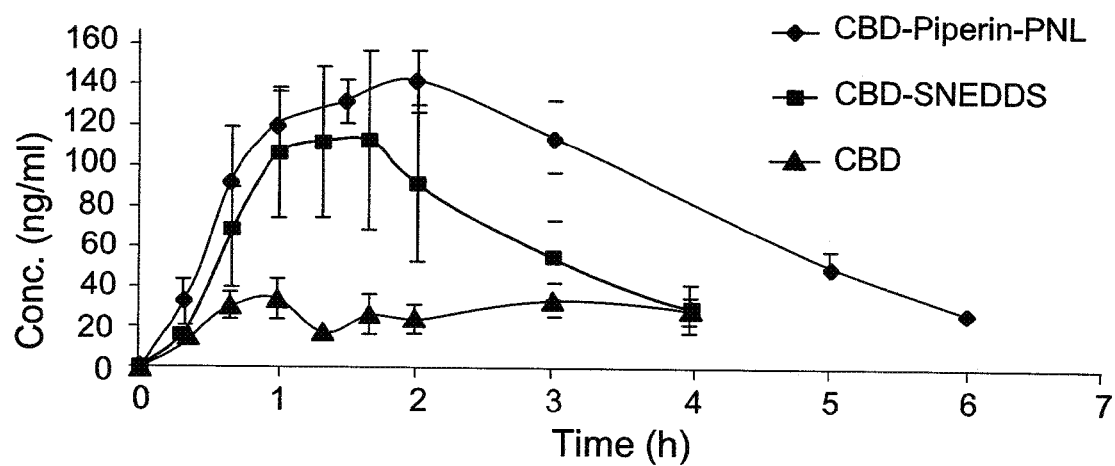
FIG. 15 presents plasma CBD concentration-time plot (mean±S.E.M.) following PO administration of CBD, CBD-PNL and CBD-Piperine-PNL to rats, CBD-15 mg/kg; Piperine 10 mg/kg (n=6 for each group). (*) Significant difference (p<0.05) from CBD corresponding value is found.

Results:

1.1 The results indicate that in rats the Piperine-PNL elevated the bioavailability of CBD by 6 fold (Table 13, FIG. 15). The contribution of the Piperine component was 2 fold increased bioavailability due to its phase-II metabolism inhibition.

TABLE 13

PK parameters (mean ± S.E.M.) derived from PO administration of CBD, CBD-PNL and CBD-Piperine-PNL 15 mg/kg; Piperine 10 mg/kg (n = 6 for each group).

| AUC (h*ng/mL) | Cmax (ng/mL) | |
| --- | --- | --- |
| 90 ± 21 | 39 ± 8 | CBD |
| 300 ± 95 (*) | 137 ± 43 (*) | CBD-PNL |
| 570 ± 23 (*†) | 170 ± 13 (*) | CBD-Piperine-PNL |

(*) Significant difference (p < 0.05) from CBD corresponding value is found
(†)Significant difference (p < 0.05) from (CBD) and (CBD-PNL) corresponding value is found.

Currently, there are limited pharmaceutical solutions in the clinical setting to overcome the absorption barriers accounted for poor oral drug availability. As mentioned hereinabove, "First pass metabolism" (both by Phase I and Phase II enzymes at the enterocyte level) and efflux transporters; P-gp hamper the oral delivery of many drugs. PNL previously developed by our group have been successfully utilized to enhance the oral absorption of drugs subjected to intraenterocyte Phase I "first-pass" metabolism and P-gp efflux. The innovation of our current approach is adding piperine into PNL.

The utilization of piperine in addition to PNL synergistically enhances bioavailability and may increase the oral absorption to greater extent than the utilization of PNL alone. The result is a platform that can be employed for:
1. Drugs which are subjected to Phase I intra-enterocyte metabolism and/or P-gp efflux.
2. Various drugs which are also directly eliminated by phase II metabolism e.g. glucuronidation process.

Thus, the present invention applies the Piperine-PNL concept to compounds suffering from significant first pass Phase I, phase II metabolism and/or P-gp efflux at the intraenterocyte level. Suitable candidates for administration in Piperine-PNL are listed in Table 14.

TABLE 14

Examples of P-gp, CYP3A4 and UDP-glucuronosyltransferase (UGT) enzymes substrates at the gut-wall and the liver, which are suitable candidates for administration in Piperine-PNL.

| | |
| --- | --- |
| Amlodipine | Calcium channel blockers |
| Diltiazem | |
| Felodipine | |
| Nicardipine | |
| Nifedipine | |
| Nimodipine | |
| Nisoldipine | |
| Verapamil | |
| Phenytoin | Antiepileptics |
| Cyclosporine | Immunosuppressants |
| Sirolimus | |
| Tacrolimus | |
| Atorvastatin | Statins |
| Lovastatin | |
| Simvastatin | |
| Fexofenadine | Antihustamins |
| Buspirone | CNS drugs |

Figure 16:
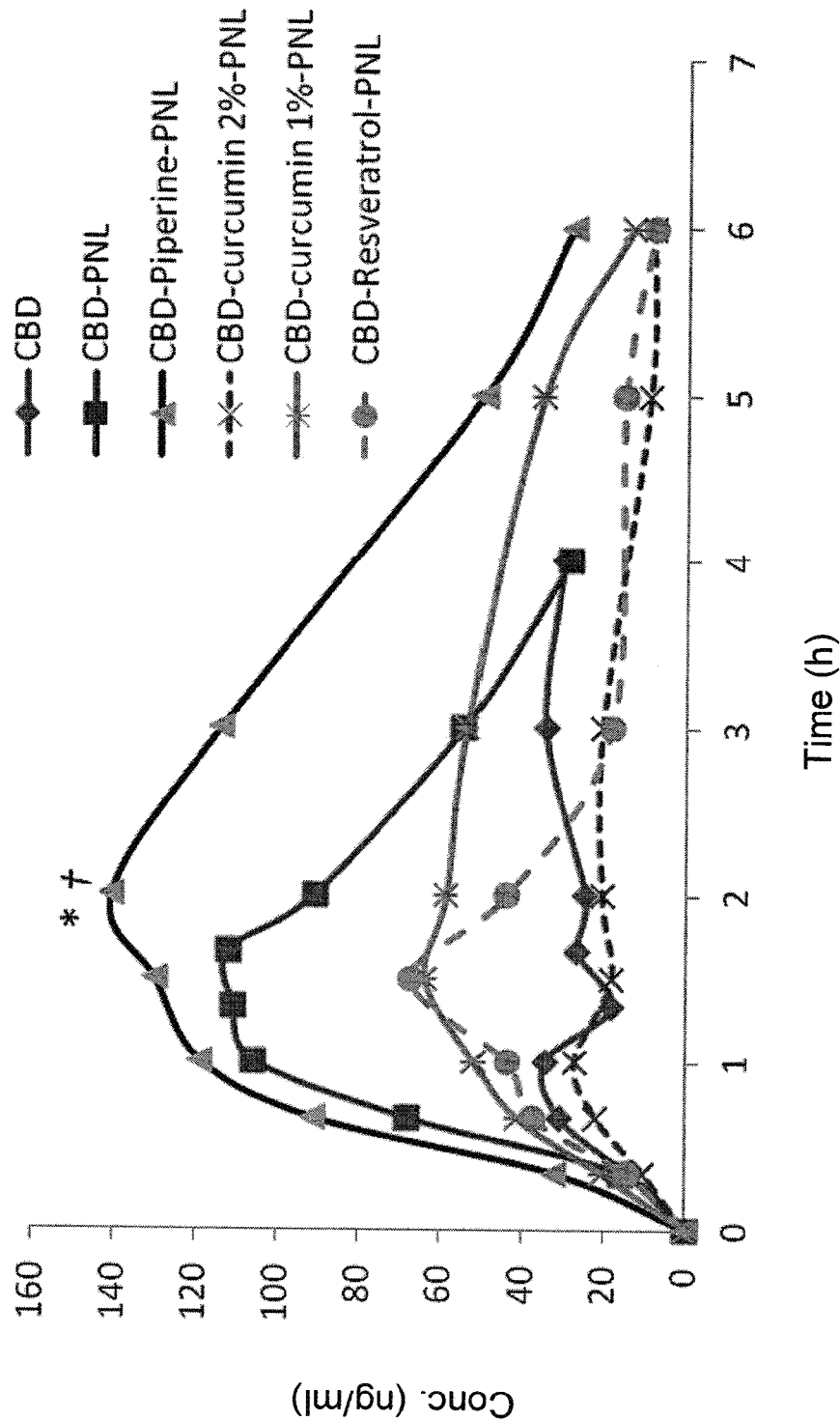
FIG. 16 presents plasma concentration vs. time plot for CBD and Cannabidiol (CBD)-PNL with and without various absorption enhancers: Resveratrol (CBD-Resveratrol-PNL), Curcumin 1% & 2% (CBD-curcumin 1%-PNL and CBD-curcumin 2%-PNL, respectively) and CBD-Piperine-PNL to rats, CBD-15 mg/kg; (n=6 for each group). *The concentration of piperine and resveratrol in the formulation was 2%; PNL—Pro-Nano-Liospheres. *CBD—Cannabidiol. (*) Significant difference (p<0.05) from CBD corresponding value is found. (†) Significant difference (p<0.05) from CBD-PNL corresponding value is found.

Results of CBD-Pro-Nano Liposheres Incorporating Curcumin, Resveratrol and Piperine as Absorption Enhancers The results in FIG. 16 and Table 15 show that administration of CBD-piperine-PNL resulted in significantly higher oral relative bioavailability in comparison to all the tested formulations, when administered to rats. Oral administration of CBD-piperine-PNL resulted in significantly higher AUC and Cmax values by 5 fold and 15 fold, respectively, as compared to control.

TABLE 15

PK parameters (mean ± S.E.M.) derived from PO administration of CBD and CBD-Piperine 2%-PNL to rats; (n = 6 for each group).

| | $C_{max}$ (ng/mL) | AUC (h*ng/mL) |
| --- | --- | --- |
| CBD | 39 ± 8 | 90 ± 21 |
| CCBD-Piperine 2%-PNL | 170 ± 13(*) | 570 ± 23(*†) |

(*)Significant difference (p < 0.05) from CBD corresponding value is found.
(†)Significant difference (p < 0.05) from (CBD-PNL) corresponding value is found.

It is noted that curcumin could not be effectively incorporated into PNL system. The incorporation of curcumin resulted in its precipitation following the introduction of the pre-concentrate (containing piperine) into the water phase in-vitro. The same effect most probably occurs in-vivo. Moreover, as the absorption of CBD following CBD-curcumin 1% or 2%-PNL is lower as compared to CBD-PNL it is reasonable to assume that the incorporation of curcumin damages the proper formation of the CBD nano-liposheres resulting in poorer oral bioavailability of CBD.

Though the incorporation of both resveratrol and piperine results in homogeneous and visually clear pre-concentrate the oral bioavailability of CBD is enhanced only when the delivery system contains piperine.

Curcumin, resveratrol and piperine were reported, in the literature, to successfully enhance the bioavailability of several lipophilic compounds. The proposed mechanisms behind this phenomenon are: CYP P450 inhybition, p-glycoprotein (p-gp) efflux reduction and inhibition of phase 2 metabolism. Due to its poor aqueous solubility, curcumin can be incorporated into the lipid Self-nanoemulsifying drug delivery systems (SNEDDS) core. This incorporation increases curcumin concentration that reaches the intestine and the liver, and competitively inhibit CBD metabolism in those metabolic sites.

Thus, incorporation of piperine into SNEDDS increases the plasma concentrations of THC and CBD.

A Selection of an Absorption Enhancer for the Development of Various Pro-Nano-Lipospheres Containing an Absorption Enhancer and Several Different Lipophilic Drugs The development of each of the formulations, in terms of a selection of the different components, was conducted by the following method. A combination of certain components was used as a reference starting point (as per Table 16). The choice of these certain triglyceride, organic amphiphilic co-solvent and the combination of surfactants in the detailed portions in Table 16 was based on the inventors' previous experience with various lipophilic drugs. Thus, an absorption enhancer was added to this specified prototype formulation to form a pre-concentrate. In case this prototype formulation was failed to efficiently dissolve the absorption enhancer or in case a precipitation of an absorption enhancer was observed following the introduction of the pre-concentrate to a water phase, a replacement of triglyceride or/and organic co-solvent was performed.

TABLE 16

Curcumin-ProNanoLipospheres development

| | % (w/w) | Pre-concentrate 1 | Pre-concentrate 2 | Pre-concentrate 3 | Pre-concentrate 4 | Pre-concentrate 5 |
|---|---|---|---|---|---|---|
| curcumin | 1  2 | ✓ | ✓ | ✓ | ✓ | ✓ |
| tween 20 | 12.5 | ✓ | ✓ | ✓ | ✓ | ✓ |
| span 80 | 12.5 | ✓ | ✓ | ✓ | ✓ | ✓ |
| lecithin | 9 | ✓ | ✓ | ✓ | ✓ | ✓ |
| HCO 40 | 12.5 | ✓ | ✓ | ✓ | ✓ | ✓ |
| ethyl lactate | 37  36 | ✓ | ✓ | ✓ | ✓ | |
| N-methyl-pyrolidone | | | | | | ✓ |
| trilaurin | 12.5 | | | | | ✓ |
| tripalmitin | 12.5 | | ✓ | | | |
| trimyristin | 12.5 | | | ✓ | | |
| tricaprine | 12.5 | ✓ | | | ✓ | |

Incorporation of curcumin into all five formulations formed a pre-concentrate in which curcumin was fully dissolved. However, upon dilution with water phase, curcumin at the concentration of 1% and 2% precipitated immediately from pre-concentrates 2, 3, 4 and 5. The same effect most probably occur in-vivo. Only pre-concentrate 1 following dilution with water phase formed a nanodispersion system which was stable, i.e. no precipitation of curcumin at the concentration of 1% and 2% was observed, for 10 min at 37° C., giving sufficient time window to perform pre-clinical studies. Thus CBD 3% was added to these formulations to form two pre-concentrates; CBD-curcumin 1%-PNL and CBD-curcumin 2%-PNL. Following introduction of these two pre-concentrates to water phase nano-dispersions were formed. No precipitation both of the active ingredient (CBD) and of the absorption enhancer (curcumin) was observed for 10 min at 37° C. following dilution. Thus CBD-curcumin 1% and CBD-curcumin 2%-PNL were tested in pre-clinical trials. The oral administration of CBD-curcumin 1% and 2%-PNL resulted in significantly lower AUC and Cmax values as compared to the oral administration of CBD-PNL to rats. Moreover, the oral administration of CBD-curcumin 1% and 2%-PNL didn't enhance the oral bioavailability of CBD as compared to the administration of CBD alone. Thus, it is reasonable to assume that the incorporation of curcumin damages the proper formation of the CBD nano-lipospheres upon introduction to water phase, i.e. the fluids of the gastrointestinal tract, resulting in poorer oral bioavailability of CBD.

TABLE 17

Resveratrol and piperine -ProNanoLiposphere development

| | % (w/w) | Pre-concentrate 1 | Pre-concentrate 2 |
|---|---|---|---|
| resveratrol | 2 | ✓ | |
| piperine | 2 | | ✓ |
| tween 20 | 12.5 | ✓ | ✓ |
| span 80 | 12.5 | ✓ | ✓ |
| lecitin | 9 | ✓ | ✓ |
| HCO 40 | 12.5 | ✓ | ✓ |
| ethyl lactate | 36 | ✓ | ✓ |
| tricaprine | 12.5 | ✓ | ✓ |

The incorporation of both resveratrol and piperine formed homogeneous and visually clear pre-concentrate. No precipitation of both resveratrol and piperine were observed upon dilution of these pre-concentrates with water. Thus CBD 3% was added to these formulations to form two pre-concentrates; CBD-resveratrol-PNL and CBD-piperine-PNL. Following introduction of these two pre-concentrates to water phase a stable and visually clear nano-dispersions were formed. No precipitation both of the active ingredient (CBD) and of the absorption enhancers (resveratrol and piperine) was observed for up to two month following dilution. Thus, these two formulations were tested in pre-clinical trials.

All the selected and tested materials curcumin, resveratrol and piperine were reported to enhance the oral bioavailability of various lipophilic compounds in-vivo, thus are referred to as "absorption enhancers". Moreover, both CBD-resveratrol-PNL and CBD-piperine-PNL showed favorable stability characteristics as compared to CBD-curcumin 1% and 2%-PNL. However, results of pre-clinical studies indicated that only CBD-piperine-PNL oral administration resulted in significant enhance in the bioavailability of CBD as compared to the administration of CBD-PNL and the administration of CBD alone.

Testing the Compatibility of Various BCS Class II and Class IV Drugs with the Pre-Concentrate:

In order to determine the compatibility of the developed PNL delivery system with various lipophilic drugs, we have tested the ability of the piperine-PNL to dissolve various BCS class II and IV drugs. Incompatibility was determined if the pre-concentrate were unable to fully dissolve the tested drug or if the tested drug-piperine-PNL were not able to self-emulsify upon gentle agitation in aqueous environment or resulted in unstable dispersion system.

TABLE 18

Testing the compatibility of various BCS class II and class IV drugs with the pre-concentrate.

| | % (w/w) | tacrolimus | amiodarone | Amphotericin B | simvastatin | cyclosporine | Tetrahydrocan-nabinol (THC) |
|---|---|---|---|---|---|---|---|
| piperine | 2 | √ | √ | √ | √ | √ | √ |
| tween 20 | 13 | √ | √ | √ | √ | √ | √ |
| span 80 | 13 | √ | √ | √ | √ | √ | √ |
| lecitin | 9 | √ | √ | √ | √ | √ | √ |
| HCO 40 | 13 | √ | √ | √ | √ | √ | √ |
| ethyl lactate | 37 | √ | √ | √ | √ | √ | √ |
| trilaurin | 13 | √ | | √ | √ | √ | √ |
| tricaprine | 13 | √ | | | | | |

Amphotericin B was found to be incompatible with the pre-concentrate. The rest of the drugs tested were found to be compatible with the pre-concentrate and upon dilution with water formed clear and transparent nano-dispersion systems with desirable range (less than 200 nm) of the size of the particles formed. CBD//CBD-THC//tacrolimus and cyclosporine piperine-PNL formed nano-dispersion systems of optimal particle size <50 nm. The exception was pre-concentrate incorporating Amiodarone which when dispersed formed particles of 276 nm (Table 18).

A Detailed Description of the Compatibility Characteristics of the Tested Compounds with the Piperine-PNL
Amphotericin-Piperine-PNL:
The drug did not dissolve in the pre-concentrate.
Cyclosporine-Piperine-PNL:
the drug was fully dissolved in the pre-concentrate. Upon dissolution of the pre-concentrate with water, a clear and transparent dispersion was formed.
THC-CBD-Piperine-PNL:
the drug was fully dissolved in the pre-concentrate. Upon dissolution of the pre-concentrate with water, a clear and transparent dispersion was formed.
Tacrolimus-Piperine-PNL:
the drug was fully dissolved in the pre-concentrate. Upon dissolution of the pre-concentrate with water, a clear and transparent dispersion was formed.
Simvastatin-Piperine-PNL:
the drug was fully dissolved in the pre-concentrate. Upon dissolution of the pre-concentrate with water, clear opal white dispersion was formed. No precipitation of the drug was observed up to 2 h post dissolution.
Amiodarone-Piperine-PNL:
the drug was fully dissolved in the pre-concentrate. Upon dissolution of the pre-concentrate with water, milky white dispersion was formed, implying an insufficiently large mean droplet size. No precipitation of the drug was observed up to 2 h post dissolution.

TABLE 19

Particle size and polydispersity index (PdI) of the different PNLs following 1:10 dilution with water. Particle size and ζ potential were determined using Zetasizer Nano ZS ZEN 3600 (Malvern Instruments Ltd, Malvern, UK).

| formulation | Size nm (diameter) | PdI |
|---|---|---|
| CBD-piperine-PNL | 30 | 0.23 |
| Cyclosporine-piperine-PNL | 26 | 0.2 |
| Simvastatin-piperine-PNL | 76 | 0.53 |
| Tacrolimus-piperine-PNL | 38 | 0.34 |
| THC-CBD-piperine-PNL | 40 | 0.25 |
| Amiodarone-piperine-PNL | 276 | 0.41 |
| CBD-resveratrol-PNL | 65 | 0.5 |

***Polysorbate 20 (Tween ® 20), Sorbitan monooleate 80 (Span ® 80), Polyoxyethylene hydrogenated castor oil 40 (HCO-40).

The invention claimed is:

1. A method for increasing the bioavailability of at least one orally administered drug in a subject in need of said drug, the method comprising orally administering to said subject:
   (1) said at least one orally administered drug, and
   (2) a composition, comprising a dispersible concentrate comprising:
      (i) a combination of surfactants selected from at least one high HLB (hydrophilic/lipophilic balance) surfactant having an HLB of at least 8, and at least one surfactant being a low HLB surfactant having an HLB of less than 5;
      (ii) at least one solid component at room temperature, the at least one solid component having a melting temperature above 25° C. and is selected from the group consisting of fatty acids, fatty acid esters, fatty amines, fatty amides and fatty alcohols; and
      (iii) an amphiphilic solvent,
   wherein the composition does not comprise curcumin and the composition comprises particles with a mean diameter of less than 100 nm when measured after the composition is dispersed in an aqueous medium;
   wherein the composition and the at least one orally administered drug are being administered separately and substantially simultaneously,
   such that upon contact of the composition and the at least one orally administer drug with gastrointestinal (GI) tract fluids, the bioavailability of said at least one orally administered drug is increased, as determined by measuring the total systemic drug concentrations over time after administration of said composition as compared to after administration of the at least one orally administered drug alone.

2. The method according to claim 1, wherein said composition is administered either less than 20 min. before, less than 20 min after or simultaneously with the at least one orally administered drug.

3. The method according to claim 1, for treatment of at least one disease or disorder.

4. The method according to claim 1, wherein said at least one orally administered drug is a cannabinoid, a derivative or a synthetic analog thereof, or a mixture of cannabinoids.

5. The method according to claim 1, wherein said at least one orally administered drug is a cannabinoid being selected from the group consisting of tetrahydrocannabinol, cannabidiol (CBD), cannabinol, cannabigerol, tetrahydrocannabivarin, cannabidivarin and cannabichromene.

6. The method according to claim 1, wherein said composition comprises a phospholipid.

7. The method according to claim 1, wherein the amphiphilic solvent is selected from the group consisting of lower alkyl esters of lactic acid, lower alkyl lactone esters and N-methylpyrrolidone.

8. The method according to claim 1, wherein the at least one high HLB surfactant having an HLB of at least 8 and the at least one low HLB surfactant having an HLB of less than 5 are selected from the group consisting of nonionic and zwitterionic compounds.

9. The method according to claim 1, wherein the at least one high HLB surfactant having an HLB of at least 8 is a sorbitan monolaurate, a polyoxyethylene or a mixture thereof.

10. The method according to claim 1, wherein the at least one low HLB surfactant having an HLB of less than 5 is a sorbitan monooleate.

11. The method according to claim 1, wherein the at least one high HLB surfactant having an HLB of at least 8 is polyethyleneglycol-hydrogenated castor oil.

12. The method according to claim 1, wherein the at least one solid component at room temperature is selected from the group consisting of mono-, di-, and triglycerides and fatty acid esters with long and short chain alcohols.

13. The method according to claim 1, wherein the at least one solid component at room temperature is selected from the group consisting of tricaprin, trilaurin, trimyristine, tripalmitin, tristearin and mixtures thereof.

14. The method according to claim 1, wherein the amphiphilic solvent is selected from the group consisting of methyl lactate, ethyl lactate, propyl lactate, spironolactone and N-methylpyrrolidone.

15. The method according to claim 1, wherein the amphiphilic solvent is combined with a hydrophilic organic solvent.

16. The method according to claim 1, wherein the amphiphilic solvent is an organic solvent.

17. The method according to claim 16, wherein the organic solvent is ethanol.

* * * * *